US005795875A

United States Patent [19]
Holme et al.

[11] Patent Number: 5,795,875
[45] Date of Patent: Aug. 18, 1998

[54] THERAPEUTIC METHODS OF USING O-DESULFATED HEPARIN DERIVATIVES

[75] Inventors: Kevin R. Holme, Alameda, Calif.; Patrick N. Shaklee, Waunakee, Wis.; Masayuki Ishihara, Alameda, Calif.

[73] Assignee: Glycomed Incorporated, Alameda, Calif.

[21] Appl. No.: 781,098

[22] Filed: Jan. 9, 1997

Related U.S. Application Data

[62] Division of Ser. No. 239,075, May 6, 1994.
[51] Int. Cl.$^6$ .......................... A61K 31/725; C08B 37/10
[52] U.S. Cl. ........................... 514/56; 514/921; 536/21
[58] Field of Search ..................... 514/56, 921; 536/21

[56] References Cited

U.S. PATENT DOCUMENTS

| | | | |
|---|---|---|---|
| 4,613,665 | 9/1986 | Larm | 536/20 |
| 4,954,637 | 9/1990 | Nitecki et al. | 548/546 |
| 4,990,502 | 2/1991 | Lormeau et al. | 514/56 |
| 5,280,016 | 1/1994 | Conrad et al. | 514/56 |
| 5,296,471 | 3/1994 | Holme et al. | 514/56 |
| 5,583,121 | 12/1996 | Chaudry et al. | 514/56 |

FOREIGN PATENT DOCUMENTS

| | | | |
|---|---|---|---|
| 51-26987 | 3/1976 | Japan | C08B 37/10 |
| 52-155690 | 12/1977 | Japan | C08B 37/00 |
| WO 92/01003 | 1/1992 | WIPO | C08B 37/10 |
| WO 92/17187 | 10/1992 | WIPO | A61K 31/725 |
| WO 92/18545 | 10/1992 | WIPO | C08B 37/10 |
| WO 93/19096 | 9/1993 | WIPO | C08B 37/10 |

OTHER PUBLICATIONS

Jaseja et al., "Novel regio–and stereoselective modifications of heparin in alkaline solution. Nuclear magnetic resonance spectroscopic evidence," Can. J. Chem. (1989) 67:1449–1456 months not available.

Rej et al., "Base–catalyzed conversion of the a–L–iduronic acid 2–sulfate unit of heparin into a unit of a–L–galacturonic acid, and related reactions," Carbohydr. Res. (1990) 200:437–447 months not available.

Nagasawa et al., "Solvolytic Desulfation of Glycosaminoglycuronan Sulfate with Dimenthyl Sulfoxide Containing Water or methanol," Carbohydr. Res. (1977) 58:47–55 months not available.

Piani et al., "Alkali–induced optical rotation changes in heparins and heparan sulfates and their relation to iduronic acid–containing sequences," J. Carbohydr Chem (1993) 12:(4&5)507–521 months not available.

Walenga et al., "In vitro evlauation of heparin fractions: Old vs. New Methods," CRC Critical Reviews in Clinical Laboratory Sciences (1986) 22(4) :361–389 month not available.

Guimond et al., "Activating and Inhibitory Heparin Sequences for FGF-2 (Basic FGF)," J. Biol. Chem (1993) 268:32:23906–23914 months not available.

Macarana et al., "Minimal Sequence in Heparin/Heparan Sulfate Required for Binding of Basic Fibroblast Growth Factor," J. Biol. Chem (1993) 268:32:23898–23905 months not available.

Aviezer et al., "Differential Structural Requirements of Heparin and Heparan Sulfate Proteoglycans That Promote Binding of Basic Fibroblast Growth Factor to its Receptor," J...Biol.Chem. (1994) 269:1:114–121 months not available.

Walker et al., "Specific Heparan Sulfate Saccharides Mediate the Activity of Basic Fibroblast Growth Factor," J.Biol.Chem. (1994) 269:2:931–935 months not available.

Ishihara et al., "Regulation of Biosynthesis of the Basic Fibroblast Growth Factor Binding Domains of Haparan Sulfate by Heparan Sulfate–N–Deacteylase/N–Sulfotransferase Expression," J.Biol.Chem. (1993) 268:27:20091–20095 months not available.

Yuen et al., "Sulfated Blood Group Lewis[1], A Superior Oligosaccharide Ligand for Human E–Selectin" J.Biol.Chem. (1994) 269:5:1595–1598 months not available.

Kosakai et al., "Sulfated Oligosaccharides Isolated from the Deamination Products of Heparins[1]" J.Biol.Chem. (1981) 89:6:1933–1944 months not available.

Matsuo et al., "A Novel regioselective desulfation of polysaccharide sulfates: Specific 6–O–desulfation with N,O–bis(trimethylsilyl)acetamide," Carbohydrate Research (1993) 241:209–215 months not available.

Ishihara et al., "A Cell–Based Assay for Evaluating the Interaction of Heparin–like Molecules and Basic Fibroblast Growth Factor," Analytical Biochem. (1992) 202:310–315 months not available.

Nagasawa et al., "Solvolytic desulfation of Glycosaminoglycuronan Sulfates with Dimethyl Sulfoxide Containing Water or Methanol," Carbhydrate Research, (1977) 58:47–55 months not available.

Nagasawa et al., "An Improved Method for the Preparation of Chondroitin by Solvolytic Desulfation of chondroitin Sulfates," J.Biochem. (1979) 86:1323–1329 months not available.

Herold et al., "Glycoprotein C of Herpes Simplex Virus Type 1 Plays a Principal Role in the Adsorption of Virus to Cells and in Infectivity," J.Virology (1991) 65:1090–1098 months not available.

Casu et al., "Retention of Antilipemic Activity by Periodate–oxidized Non–anticoagulant Heparins," Arzneim Forsch/Drug Res (1986) 36:(1)4:637–642 months not available.

(List continued on next page.)

*Primary Examiner*—Kathleen K. Fonda
*Attorney, Agent, or Firm*—Lyon & Lyon LLP

[57] ABSTRACT

Compositions and methods of making selectively O-desulfated heparin compositions, preferably 6-O-desulfated heparin compositions, wherein the methods permit regulating the degree of 6-O-desulfation. The compositions are useful for treating various diseases, including cancer, angiogenesis, shock, ischemia reperfusion injury, inflammation, and cardiovascular diseases including restenosis.

16 Claims, 11 Drawing Sheets

OTHER PUBLICATIONS

Inoue et al., "Selective N–Desulfation of Heparin with Dimethyl Sulfoxide Containing Water or Methanol," Carbohydrate Research (1976) 46:87–95 months not available.

Kosakai et al., "Ester Sulfates in Sulfated Oligosaccharides from the Deamination Products of Porcine Heparin and Whale Heparin," Chemistry and Biology of Heparin (1979) 97–104 months not available.

Usov et al., "Solvolytic desulphation of sulphated carbohydrates," Carbohydrate Res. (1971) 18:336–338 months not available.

Kosakai et al., "Isolation and Characterization of Sulfated Disaccharides from the Deamination Products of Porcine Heparin (α–Heparin) and Whale Heparin (w–Heparin), and a Comparison of the Deamination Products[1]," J.Biochem. (1978) 83:1567–1575 months not availble.

Ishihara, et al., "Preparation of Affinity–fractionated, Heparin–derived Oligo–saccharides and Their Effects on Selected Biological Activities Mediated by Basic Fibroblast Growth Factor," J. Biol. Chem. (1993) 268:7:4675–4683 months not available.

Kazatchkine, "Structural Determinants of the Capacity of Heparin to Inhibit the Formation of the Human Amplification C3 Convertase," J. Clin. Invest. (1981) 67:223–228 months not available.

Guo et al., "The Disaccharide Composition of Heparins and Heparan Sulfates[1]," Analyt. Biochem. (1989) 176;96–104 months not available.

Guo et al., "Analysis of oligosaccharides from heparin by Reversed–Phase Ion–Pairing High–performance Liquid Chromatography[1]," Analyt. Biochem. (1988) 168:54–62 months not available.

Shively, et al., "Formation of Anhydrosugars in the Chemical Depolymerization of Heparin," Biochem. (1976) 15:18:3932–3942 months not available.

Svhan et al., "Inhibition of angiogenesis by heparin fragments in the presence of hydrocortisone," Carbohydrate Polymers (1992) 18:9–16 months not available.

Castellot, Jr., et al "Heparin Potentiation of 3T3–Adipocyte Stimulated Angiogenesis: Mechanisms of Action on Endothelial Cells," J. Cell. Physio. (1986) 127:323–329 months not available.

Conrad et al., "Structural Analysis of Periodate–Oxidized Heparin," Heparin and Related Polysaccharides (1992) 31–37 months not available.

Fransson et al., "Periodate Oxidation and Alkaline Degradation of Heparin–Related Glycans," Carbohydrate Research (1980) 80:131–145 months not available.

Fransson et al., "Relationship Between Anticoagulant Activity of Heparin and Susceptibility to Periodate Oxidation," FEBS Letters (1979) 971:119–123 months not available.

Mitchell, et al., "Inhibitors of Angiogenesis," Annual Reports in Medicinal Chemistry (Academic Press 1992) 27:139–148 months not available.

Odegard et al., "Antifactor Xa Activity Measured with Amidolytic Methods," Haemostasis (1976) 5:265–275 months not available.

Hirsh et al., "Low Molecular Weight Heparin," Blood (1992) 79:1:1–7 months not available.

Wright,Jr. et al. "Structural Determinants of Heparin's Growth Inhibitory Activity: Interdependence of Oligosaccharide Size and Charge," J. Biol. Chem. (1989) 264:3:1534–1542 months not available.

Takano et al., Abstract from the Annual Meeting of the Japanese Biochem. Society (1993) 65:8:694, Abstract No. 1836 months not available.

Takashige et al., Abstract from the Annual Meeting of the Japanese Biochem. Society (1993) 65:8:694, Abstract No. 1835 months not available.

Austin, et al., "Intimal Proliferation of Smooth Muscle Cells as an Explanation for Recurrent Coronary Artery Stenosis After Percutaneous Transluminal Coronary Angioplasty," J. Am. Coll. Cardiol. (1985) 6:2:369–375 months not available.

Castellot, Jr., et al. "Heparin Potentiation of 3T3–Adipocyte Stimulated Angoigenesis: Mechanisms of Action on Endothelial Cells," J. Cell Physiol. (1986) 127;323–329 months not available.

Gershenson et al., "Tyrosine Transaminase Induction by Dexamethasone in a New Rat Liver Cell Line," Science (1970) 170:859–861 months not available.

HEPARIN

COMPOSITION IA (i)

THERAPEUTIC METHODS OF USING O-DESULFATED HEPARIN DERIVATIVES

This is a division of application Ser. No. 08/239,075 filed May 6, 1994 hereby incorporated by reference in its totality (including drawing).

FIELD OF THE INVENTION

This invention relates to O-desulfated heparin compositions and methods of making the same, preferably 6-O-desulfated heparin compositions, wherein the methods permit regulating the degree of 6-O-desulfation. The compositions are useful for treating various diseases, including cancer, angiogenesis, shock, ischemia reperfusion injury, inflammation, and cardiovascular diseases including restenosis.

ABBREVIATIONS

The following abbreviations are used for monosaccharides or for monosaccharide residues included in oligomers: D-glucuronic acid=GlcA; L-iduronic acid=IdoA; D-glucosamine =GlcNH$_2$; N-acetyl-D-glucosamine=GlcNAc; D-glucosamine N-sulfate=GlcNS; 2,5-anhydromannose=Aman; 2,5-anhydromannitol=AManH.

Abbreviations that are used to denote disaccharide residues obtained in the analysis of heparin compositions described herein are as follows: ISMS is defined as IdoA (2-sulfate)→AManH (6-sulfate); GMS$_2$ is defined as GlcA→AManH (3,6-disulfate); IS is defined as IdoA (2-sulfate)→AManH (6-sulfate)+IdoA (2-sulfate)→AManH.

In designating each saccharide residue, below the appropriate abbreviation, the location of the O-linked sulfate residues is indicated by "S" and the number of the position of sulfation where the sulfate residue is linked to oxygen on the sugar residue. In the designations for heparin structure, also, the positions involved in the alpha and beta anomeric linkages are as those conventionally found in heparin, α (glucosamine→uronic) and β (uronic→glucosamine), and the D or L configurations as conventionally found pertains. The locations of the sulfates are shown below the abbreviation for the sugar to which they apply, thus, for example,

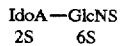

refers to a disaccharide composed of L-iduronic acid and D-glucosamine N-sulfate-linked β(1–4) with sulfates connected respectively at the 2 and 6 positions of the sugar residues.

BACKGROUND

Heparin

Heparin/heparan sulfate is a member of a class of polysaccharides known as glycosaminoglycans (GAG). These materials are copolymers of alternating hexosamine and aldouronic acid residues which are found in sulfated forms and are synthesized as proteoglycans. In the compositions of interest herein, heparin sulfate and heparin, the hexosamine which predominates is N-acetylated or N-sulfated glucosamine (GlcNAc and GlcNS). The aldouronic acid is mostly L-iduronic in heparin and mostly D-glucuronic acid in heparan sulfate. Heparan sulfate is commonly considered to have a higher proportion of glucuronic acid than heparin.

Problems of heterogeneity in preparations of heparan sulfate or heparin isolated from tissues make sharp distinctions difficult. Conventional heparin (used as an anticoagulant) has a molecular weight of 5–25 kd and is extracted as a mixture of various chain lengths by conventional procedures. These procedures involve autolysis and extraction of suitable tissues, such as beef or porcine lung, intestine, or liver, and removal of nonpolysaccharide components. The molecular weight of the chains in the extract is significantly lower than the 60–100 kD known to exist in the polysaccharide chains of the heparin proteoglycan synthesized in the tissue. The GAG moiety is synthesized bound to a peptide matrix at a serine or threonine residue through a tetrasaccharide linkage region of the sequence D-GlcA-D-Gal-D-Gal-D-Xyl→protein, which is then elongated at the D-GlcA residue with alternate additions of GlcNAc and GlcA. The polymer undergoes epimerization at certain of the GlcA residues to give IdoA, and subsequent sulfation.

Due to their chemical similarity, isolated "heparin" may contain considerable amounts of what might otherwise be classified as heparan sulfate.

Modified Desulfated Heparins

Several investigators have described the preparation of desulfated heparin. These methods for the preparation of desulfated heparin can be divided into three broad categories, (a) alkaline O-desulfation, (b) acid catalyzed desulfation, and (c) solvolytic desulfation.

(a) Alkaline O-desulfation Alkaline treatment of heparin under various conditions has been reported to result in the loss of O-sulfate groups. Jaseja et al. (*Can. J. Chem.* (1989) 67:1449) described in detail the effect of a mild alkaline treatment of beef lung heparin. Three distinct transformations were described, all of which specifically involved transformations of the 2-O-sulfated IdoA residues. Additional reports (Rej, R. N. et al., *Carbohydr. Res.* (1990) 200:437, Piani, S., et al., *J. Carbohydr. Chem.* (1993) 12(4&5):507) have confirmed and expanded upon these initial observations regarding alkaline treatment of heparin. The heparin derivatives obtained from alkaline-treated heparin are clearly distinct from the derivatives reported here since the transformations center specifically around the 2-O-sulfate group on the iduronic acid residues.

The co-owned U.S. Pat. No. 5,296,471, issued on Mar. 22, 1994, describes alkaline treatment of heparin to obtain 2-O, 3-O-desulfated heparin and its derivatives. These heparin derivatives obtained from alkaline-treated heparin are clearly distinct from the derivatives reported here since the transformations center specifically around the 2-O-sulfate on the IdoA residues and the 3-O-sulfate groups on the GlcN residues.

(b) Acid Catalyzed Desulfation The hydrolysis of sulfate substituents under acid-catalyzed conditions is well known. The rate of sulfate hydrolysis for monosaccaharides was shown to be secondary equatorial hydroxyl>secondary axial hydroxyl>primary hydroxyl (Rees, D. A., *Biochem. J.* (1963) 88:343). For heparin it has been reported that treatment under acidic conditions (0.1M HCl at 70° C.) results in the loss of sulfate groups in the order N-S>>2-O-S>6-O-S with the rate of 2-O-S loss being five times that of the 6-O-S (Shively, J. E. et al., *Fed. Proc.* (1977) 36:28 and Kosakai, M. et al., *J. Biochem* (1979) 86:147). Acid-catalyzed desulfation of heparin also results in some depolymerization of the molecule depending on the specific conditions.

(c) Solvolytic desulfation Solvolytic desulfation of heparin was reported (Inoue Y. et al., *Carbohydr. Res.* (1976) 46:87) as a method for selectively N-desulfating heparin. It was demonstrated that virtually complete hydrolysis of N-sulfate groups could be achieved with minimal loss (<20%) of O-sulfate groups and minimal depolymerization. It was also shown that complete removal of N-sulfates resulted in reduction of anticoagulant activity to less than 1% of the starting heparin. In a subsequent report (Nagasawa, K., et al., *Carbohydr. Res.* (1977) 58:47) solvolytic conditions at elevated temperatures (80°–1100° C.) were shown to be useful for desulfating glycosaminoglycans including heparin. The conditions involved heating pyridinium salt of heparin in 1–10% methanol-DMSO or 1–10% water-DMSO at 80°–1000° C. In another report the reaction medium was 2% pyridine-DMSO as described by Usov for solvolytic desulfation of sulfated polysaccharides from seaweed (Usov A.I., et al., *Carbohydr. Res.* (1971) 18:336). The result from this study demonstrated that complete N-desulfation was rapidly achieved, and that the N-desulfated material proceeded to O-desulfate at a much slower rate. When N-desulfated material was isolated and N-reacetylated prior to solvolytic treatment at 100° C., the O-desulfation went to completion more rapidly (~1 h vs >24 h). These results suggested that interaction between the liberated amine group and the sulfate esters resulted in a reduced rate of O-desulfation. Time course reactions monitoring total sulfate loss were described for solvolytic conditions including 1, 5 and 10% methanol-DMSO at 100°, 10% methanol-DMSO at 80 and 110° C., and for 1, 5 and 10% water-DMSO at 100°, 10% water-DMSO at 80 and 110° C. The products were not characterized with regard to composition or biological activity, nor was there any discussion relating to selectivity in the reaction.

The solvolytic N-desulfation method was also described in a Japanese Patent 51-26987 and the solvolytic method for N and O-desulfation was described in Japanese Patent 52-155690. It is noteworthy these Patents (particularly 52-155690) did not discuss any selectivity in O-desulfation, composition of specific partially O-desulfated products, N-resulfation of the N and O-desulfated products, or biological activities associated with completely or partially O-desulfated compositions from solvolysis.

Yosizawa has published a series of articles on the sulfation patterns in heparins and on the subject of solvolytic desulfation of heparin (Kosakai, M., et al., *J. Biochem.* (1978) 83:1567, Kosakai M., et al., *J. Biochem.* (1979) 86:147 and Kosakai, M., et al., "*Chemistry and Biology of Heparin*" (1979) pp 97–104). In one report (Kosakai, M. et al., *J. Biochem.* (1979) 8:147) porcine heparin was subjected to solvolytic conditions including 2% pyridine-DMSO at 100° C. for 9 h. The products were characterized after depolymerization by treatment with nitrous acid and oligosaccharide analysis by paper electrophoresis and ion-exchange chromatography (Kosakai, M., et al., *J. Biochem.* (1978) 83:1567). The results showed that 0.83 mol O-sulfate per glucosamine was lost (excluding the N-sulfate group which was completely lost, accounting for about 40% of total O-sulfate), and that the relative loss of 6-O-sulfate from glucosamine was greater than the loss of 2-O-sulfate from L-iduronic acid. N-resulfation (Lloyd et al., *Biochem. Pharmacol.* (1971) 20:637) of the isolated product yielded a partially O-desulfated heparin having 110 U/mg anticoagulant activity, or about 60% of the activity of the starting heparin. The authors concluded that (1) the 6-O-sulfate substituents on glucosamine do not play a significant role in the anticoagulant activity, and (2) 2-O-sulfates on iduronic acid are important for anticoagulant activity since significant loss results in decreased activity. They related the reduced anticoagulant activity of their product mainly to the small reduction in 2-O-sulfate content not to the more extensive loss of 6-O-sulfate. No conclusions were drawn regarding the effect of solvolysis on the 3-O-sulfate on select glucosamine residues since its presence and importance was not known when these studies were performed.

A key aspect of the instant invention, which distinguishes it from the work of Yosizawa (Kosakai., M. and Yosizawa, Z. "*Chemistry and Biology of Heparin*" (1989) 67:1449), is the more extensive loss of anticoagulant activity relative to the Yosizawa composition, which retained 60% of the anticoagulant activity of the starting heparin. The invention compositions have <30%, preferably <15%, of the anticoagulant activity of the starting heparin. An additional distinguishing feature is the observation by Yosizawa et al., that significant reduction of anticoagulant activity required substantial loss of 2-O-sulfate substituents from iduronic acid residues. However, the compositions characterized in this invention establish that extensive loss of 6-O-sulfate substituents (<34% of total 6-O positions of disaccharide residues are sulfated), along with comparatively minor loss of other O-sulfate groups (up to 67% of total 2-O positions of disaccharide residues are sulfated) does result in substantial reduction of the anticoagulant activity.

Solvolytic conditions have been used and reported in a number of heparin related studies for preparing N-desulfated, completely O-desulfated N-resulfated or N-reacetylated derivatives. A number of reports (Eldor, A. et al., *Blood* (1987), 70:551, Kazatchkine, M.D. et al., *J. Clin. Invest* (1981) 67:223, Ishihara, M.et al., *Anal. Biochem.* (1992) 202:310, Wright ,T. C. Jr. et al., *J. Biol. Chem.* (1989) 264:1534, and Svahn, C. M. et al., *Carbohydr. Polym.* (1992) 18:9) have shown that N-desulfated heparin derivatives tend to have significantly reduced heparin-like biological activities. N,O-desulfated N-resulfated and N,O-desulfated-N-reacetylated heparin lack bFGF binding activity. Completely O-desulfated compounds have also been examined in a number of biological systems in order to determine the importance of O-sulfate groups for activity. These data clearly distinguish the previously reported N, O-desulfated heparin derivatives from those described in this patent application.

Recently, a method has been reported to achieve selective 6-O-desulfation of a variety of mono and polysaccharides using N, O-bis-(trimethylsilyl)acetamide and related silylating agents (Matsuo, M. et al., *Carbohydr. Res.* (1993) 241:209). As for solvolysis, the compounds are converted into their pyridinium salt form and then heated at 80° C. in DMSO solution containing the silylating reagent. Among the polysaccharides treated using this method were the glycosaminoglycans dermatan sulfate and chondroitin sulfate. The mechanism is not clear, although the authors have done a number of experiments to suggest it is not simply a form of solvolytic desulfation. Takano et al. (Takano, R. et al., *Annual Meeting of the Japanese Biochemical Society* (1993) 65(8): No.1836) reported regioselective desulfation of various polysaccharide sulfates including funoran, chondroitin sulfate, dermatan sulfate and heparin using 4-(trimethylsiloxy)-3-penten-2-one (TPENON) as the silylating agent. Treatment of both chondroitin sulfate and dermatan sulfate resulted in 6-O and 4-O-desulfation, while treatment of heparin resulted in 6-O, 2-O and N-desulfation. It is noteworthy that no selective desulfation of heparin was observed under the conditions reported by the authors. Takashige et al. (Takashige, K. et al., *Annual Meeting of the Japanese Biochemical Society* (1993) 65(8): No.1835) described selective desulfation of sulfated monosaccharides, no mention was made of desulfation of sulfated polysaccharides.

It is further noteworthy that although the above references describe heparin compositions that are 6-O desulfated, and methods to produce such compositions, they do not show a method to control the degree of 6-O desulfation, nor do they show or suggest methods for producing compositions that can be variably desulfated including compositions wherein <34% of total 6-O positions and up to 67% of total 2-O positions of disaccharide residues are sulfated.

Non-Aknticoagulant Heparin

There is a body of art that describes the production of non-anticoagulant (NAC) heparin. Most of the publications describe non-anticoagulant heparin produced from depolymerized heparin/heparan sulfate, and separation of products by size. In a generally used procedure, the heparin starting material is depolymerized in the presence of nitrous acid with or without pretreatment to remove N-acetyl groups from any GlcNAc residues present. Nitrous acid, under the appropriate conditions, cleaves at the linkage between a GlcNS or GlcNH$_2$ residue and the uronic acid residue through which it is linked through a glucosamine $\alpha(1-4)$ uronic acid linkage. If the heparin has been N-deacetylated, all of the glucosamine→uronic acid residues are susceptible and complete depolymerization results in disaccharides. If the heparin has not been N-deacetylated, the glucosamine→uronic acid residues wherein the glucosamine is acetylated are resistant, and both disaccharides and tetrasaccharides and small amounts of higher oligosaccharides containing the resistant linkage result. In all cases, the glucosamine residue at the reducing terminus of the disaccharide or tetrasaccharide is converted to a 2,5-anhydromannose in the course of cleavage. This residue may further be reduced to the corresponding 2,5-anhydromannitol. These methods have been described by Bienkowski, M. J. and Conrad, H. E., *J Biol Chem* (1985) 260:356–365; Guo, Y., et al., *Anal Biochem* (1988) 168:54–62; and Guo, Y. and Conrad, H. E., *Anal Biochem* (1989) 176:96–104. These latter methods are useful in analyzing the structure of heparin and in assessing the results of various treatments of the heparin chains. Further, there have been considerable attempts to use the products of degradation of heparin from both complete and partial digestion with nitrous acid as described in the foregoing papers, or from heparinase digestion or from periodate oxidation followed by β-elimination. All of these processes can generate low molecular weight heparins for therapeutic use.

An example of non-anticoagulant depolymerized low molecular weight heparin is described in U.S. Pat. No. 4,990,502. It shows the treatment of heparin with periodate, followed by depolymerization with base, and reduction of the aldehydes generated in the periodate treatment. The resulting material is said to contain a mixture of polymers containing 17–33 residues and containing a multiplicity of residues of the formula

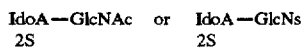

wherein the glucosamine residue is sulfated at the 3 and/or 6 position in an arbitrary manner, and wherein some of the IdoA residues may be replaced by cleaved IdoA or GlcA residues resulting from the periodate oxidation. These shortened polymeric chains are said to lack the binding site for ATIII but to be capable of inhibiting smooth muscle proliferation and to have physiological activities that include acceleration of tissue repair, prevention of atherogenous lesions, and prevention of the development of metastasis.

Treatment of heparin/heparan sulfate with periodate has also been reported by others. For instance, Fransson, L. A. and Lewis, W., *FEBS Lett* (1979) 97:119–123, describe a variety of conditions relating to the treatment of heparin/heparan sulfate with periodate and reduction by sodium borohydride or fragmentation in alkaline medium. Further, Fransson, L. A. et al., *Carbohydrate Res* (1980) 80:131–145, studied the chemistry of various forms of heparin produced with periodate. In one study, the treatment with periodate is followed by B-elimination in base to produce fragmentation. They further reported the treatment of heparin with periodate followed by partial acid hydrolysis which results in fragmentation of the chains and partial destruction of the functional groups.

Another example of a non-anticoagulant heparin is described by Casu, B. et al., *Arzneim Forsch/Drug Res* (1986) 36:637–642. They studied the effect of periodate oxidation on the anti-lipemic (lipoprotein lipase-releasing) activity of heparin. In this study, the heparin was oxidized with periodate and the products were reduced with borohydride.

PCT/SE92/00243 shows a non-anticoagulant heparin that has a molecular weight larger than the heparin starting material, and that is produced by periodate oxidation, partial depolymerization by alkali, and subsequent borohydride reduction.

WO 93/19096 shows oligosaccharides having a high specific binding affinity for FGF growth factors wherein the oligosaccharides are made up of 10–14 disaccharide units, which include disaccharide units composed of an N-sulfated glucosamine residue and a 2-O-sulphated iduronic acid residue. The oligosaccharides are produced from heparan sulphate of human fibroblast heparan sulfate proteoglycan by enzymatic depolymerization with heparitinase, wherein the 6-O GlcN position is <20% sulfated, and the 2-O IdoA position is 100% sulfated.

Maccarana et al. (Maccarana et al., *J. of Biol. Chem.*, (1993) 268:23898, Guimond et al., *J. of Biol. Chem.*, (1993) 268:23906) have described the interactions between bFGF and heparin/heparan derived oligosaccharides. The oligosaccharides are produced by fragmentation of native and partially desulfated heparin/heparan sulfate, including heparin wherein about one third of the 2-O-sulfate groups are lost and all the 6-O-sulfate groups are lost. It is noteworthy that the 6-O-positions were completely desulfated, unlike the composition described in the instant application wherein upto 34% of the total 6-O-positions and upto 67% of the total 2-O-positions are sulfated.

Finally, the 2-O desulfated heparin compositions described by Jaseja, M., et al., in *Can. J. Chem.* (1989) 67:1449–1456, have reduced anticoagulant activity.

It is important to note, that although non-anticoagulant heparins are known in the art, the art does not teach a method for producing substantially non-anticoagulant heparins wherein about <34% of total 6-O positions and up to 67% of total 2-O positions of disaccharide residues are sulfated.

Biological Properties of Non-Anticoagulant Heparins

Aside from their non-anticoagulant activity, NAC heparins have certain other novel biological properties. Some of these are described below.

Inhibition of Heparanase

The metastatic spread of tumor cells throughout the body is thought to be facilitated by enzymes secreted by tumor cells that degrade components of the basement membrane, thereby allowing tumor cells to disseminate via the circulation. One such enzyme is endo-β-D-glucuronidase, or heparanase, which degrades heparan sulfate glycosaminoglycans. Heparan sulfate is a prominent component of parenchymal cell basement membranes.

PCT patent application, WO 92/01003, shows that certain non-anticoagulant heparins act as heparanase inhibitors, and that they may be effective in lessening or preventing lung colonization by metastatic cell variants. The non-anticoagulant heparins were prepared from heparin by N-desulfation followed by N-acetylation, or N,O desulfation followed by N-resulfation. It is noteworthy that these heparin derivatives were completely O-desulfated, unlike compositions of the instant invention, which are partially O-desulfated.

Inhibition of Angiogenesis

Angiogenesis is the process whereby new blood vessels are produced. It is a process that may be associated with certain diseases, including arthritis, and the growth and metastasis of tumors. See, Mitchell and Wilks, *Annual Reports in Medicinal Chemistry* (Academic Press 1992) 27:139.

Compounds that stimulate or inhibit angiogenesis can be identified using several assays known in the art. Perhaps the easiest assay to use is the chicken chorioallantoic membrane (CAM) assay. With this assay it has been shown that certain heparinoids inhibit angiogenesis when administered with certain angiostatic steroids. Folkman and Ingber, *Ann. Surg.* (1987) 206:374, Folkman et al., *Science* (1983) 221:719.

Inhibition of bFGF

Heparin or certain NAC heparins are known to bind bFGF with concomitant modulation of bFGFs mitogenic activity. The bFGF binding properties of certain heparins or heparin like molecules are described in this publication. For example, compositions having anticoagulant activity of 5–15% retain sufficient 2-O-sulfate substituted iduronic acid residues to maintain the ability to inhibit binding of bFGF to heparan sulfate ($IC_{50}$–2 µg/ml) chains on RO-12 UC cells in a manner almost equivalent to heparin ($IC_{50}$–1µg/ml). This ability to interact with bFGF in a heparin-like manner indicates that bFGF-related heparin activities are substantially retained, particularly for compositions having anticoagulant activity of 5–15% and at least 28%, and preferably 49% of the 2-O-sulfate content. Compositions having more extensive 2-O-sulfate loss show a unique trend with respect to their cell growth inhibition and cell growth stimulation properties. Certain compositions show a reduced ability relative to heparin to inhibit bFGF-dependent cell growth, but have virtually equivalent ability to stimulate bFGF-dependent cell growth. This unexpected trend toward selectivity of bFGF-stimulatory activity suggests certain compositions may be useful as selective agents for the stimulation of angiogenesis, neovascularization, revascularization, collateral development and wound healing.

Assays for measuring the effect of heparinoids on bFGF are known in the art. A cell based competitive binding assay is described by Ishihara, M., et al., *Anal Biochem* (1992) 202:310–315.

Platelet Inhibition

Heparin's best known property is its anticoagulant activity, which is evidenced by the ability of heparin to prolong the bleeding time in animals. This occurs because heparin binds to the protease pro-inhibitor antithrombin III via its specific antithrombin III binding region. This, in turn, ultimately blocks the blood clotting cascade. Heparin is also known to have an anti-thrombotic effect, and at least in part this is a result of heparin's capacity to inhibit platelet aggregation. Interference with platelet aggregation causes a significant bleeding liability in some patients. Certain NAC heparins exhibit both non-anticoagulant activity and inhibit platelet aggregation. See, for example, co-owned U.S. patent application, Ser. No. 753,299, filed Sep. 3, 1991, or PCT Patent Application No. US92/02516, filed Mar. 27, 1992.

Antithrombotic Activities

The anti-Xa activity of heparin and heparin derivatives is measured using a chromogenic assay (Odegard, O. R., et al., *Haemostasis* (1976) 5:265, and Walenga, J. M., et al., *CRC Critical Reviews in Clinical Laboratory Sciences* (1986) 22(4):361). Derivatives from unfractionated heparins have substantially reduced activity than that of the starting heparin. This activity reduction suggests a reduced affinity of these compositions for ATIII, the main inhibitory pathway for Factor Xa.

The anti-IIa activity of heparin and heparin derivatives is measured using an assay kit and a chromogenic substrate (Walenga, J. M., et al., *CRC Critical Reviews in Clinical Laboratory Sciences* (1986) 22(4):361). Derivatives from unfractionated heparins have substantially reduced activity than that of the starting heparin. This would indicate that these compositions have lost affinity for both ATIII and Heparin Cofactor II, the two main mechanisms for inhibition of Factor IIa.

Inhibition of smooth muscle cell proliferation

Proliferation of smooth muscle cells in blood vessel walls occurs in response to vascular injury, and in association with certain disease states (Austin, G. E., et al., *J Am Coll Cardiol* (1985) 6:369–375). The proliferation of these cells can have negative effects due to the production of excess proteins or other matrix molecules, which, along with the cells themselves, form pathologic lesions of, for example, atherosclerosis, renal hypertension, pulmonary hypertension, vasculitis, and post-surgical vascular restenosis. Thus, heparin/heparan sulfate has applications in the treatment of these diseases.

Inhibition of Shock

Certain NAC heparins are also useful for treating a certain form of shock, hypovolemic shock and related syndromes. In general, hypovolemic shock can be described as widespread hypoperfusion of cells and tissue due to reduction in blood volume or cardiac output or redistribution of blood resulting in an inadequate effective circulating volume.

Hypovolemic shock, and models for studying this condition are described by Chaudry and Ayala in "Immunological Aspects of Hemorrhage" (R. G. Landes Co., Austin, Tex., 1992).

An analogous series of events is associated with septic shock except, and most critically, the key mediators of the inflammatory response are unlikely to be the same as those that cause hypovolemic shock. The initial blood volume reduction in septic shock occurs as a result of blood pooling after endotoxin stimulated neutrophil activation and the release of inflammation mediating cytokines (TNF, IL-1 and IL-6, IL-10, TGF-β etc.).

It is important to keep in mind that hypovolemic and septic shock are distinct diseases. Hypovolemic shock is a general collapse of the circulatory system that can be caused by many events including any trauma to the circulatory system (e.g. gun shot wound, automobile injury, burns, stabbing, and so on). Septic shock, on the other hand, is caused by bacterial infection. Thus, as mentioned above, the causes of these diseases are highly likely to be distinct.

Ischemia/reperfusion injury (I/RI) is another instance where inflammation mediated cell and organ damage result after a reduced blood flow state (ischemia).

The vascular damage associated with hypovolemic shock, and the resulting infiltration of neutrophils and leukocytes into the various organs leads to tissue damage and ultimately multiple organ failure (MOF) and acute respiratory distress syndrome (ARDS). The destructive agents and mediators are numerous and include cytokines, enzymes and various other inflammatory agents. MOF and ARDS can occur in severe shock and often result in death. For therapeutic agents to be effective in shock, they must protect the microvasculature and various organs (liver, kidney, heart, spleen and gut) from failure. The importance of protecting or restoring gut function and intestinal function in hemorrhagic shock and I/R injury has been reported, and correlates with reduced septic complications, and long-term survival.

SUMMARY OF THE INVENTION

In one aspect, the invention is directed to methods of O-desulfating heparin, preferably to produce 6-O-desulfated heparin compositions. The methods permit controlling the degree of 6-O-desulfation such that compositions can be produced that have a desired amount and distribution of sulfation.

A second aspect of the invention is directed to substantially non-fragmented heparin compositions wherein about <34% of total 6-O positions of disaccharide residues are sulfated, in conjunction with partial loss of other O-sulfate groups (up to 67% of total 2-O positions of disaccharide residues are sulfated). The compositions have the following unique properties; substantial anti-cancer activity, substantially no anticoagulant activity, inhibition of platelet aggregation, inhibition of bFGF binding to heparan sulfate and inhibition of heparanase and angiogenesis.

A third aspect of the invention is directed to substantially non-fragmented heparin compositions wherein about 12–26% of total 6-O positions and about 28–50% of total 2-O positions of disaccharide residues are sulfated.

A fourth aspect of the invention is directed to substantially non-fragmented heparin compositions wherein <13% of total 6-O positions and about 14–28% of total 2-O positions of disaccharide residues are sulfated.

A fifth aspect of the invention is directed to 6-O desulfated heparin fragments or heparin fragments wherein the degree of 6-O-desulfation can be controlled such that compositions having a desired amount and distribution of sulfation can be produced.

A sixth aspect of the invention is directed to methods of producing substantially unfragmented 6-O-desulfated heparin compositions from heparin, wherein the degree of 6-O-desulfation can be controlled such that compositions having a desired amount and distribution of sulfation can be produced, the preferred method consisting of desulfating heparin, substantially completely at the N-sulfate positions, and selectively at the 6-O and 2-O positions, followed by N-resulfation at the amino position.

A seventh aspect of the invention is a description of methods of making compositions of 6-O-desulfated heparin fragments from heparin, wherein the degree of 6-O-desulfation can be controlled such that compositions having a desired amount of sulfation can be produced, via a solvolytic desulfation reaction, involving the conversion of heparin into a pyridinium salt form, followed by N-desulfation and 6-O-desulfation and subsequent N-resulfation.

An eighth aspect of the invention is directed to methods of producing 6-O-desulfated heparin fragments, wherein the degree of 6-O-desulfation can be controlled such that compositions having a desired amount of sulfation can be produced via a solvolytic desulfation reaction.

A ninth aspect of the invention is directed to methods of preventing or treating disease, including restenosis, cancer, angiogenesis, shock, ischemia reperfusion injury, inflammation, and cardiovascular diseases, by administering to an animal host compositions of substantially unfragmented 6-O-desulfated heparin, or 6-O-desulfated heparin fragments.

These and other aspects of the invention will be more fully understood upon a detailed consideration of the invention presented below. dr

MODES OF CARRYING OUT THE INVENTION

Figure 1:
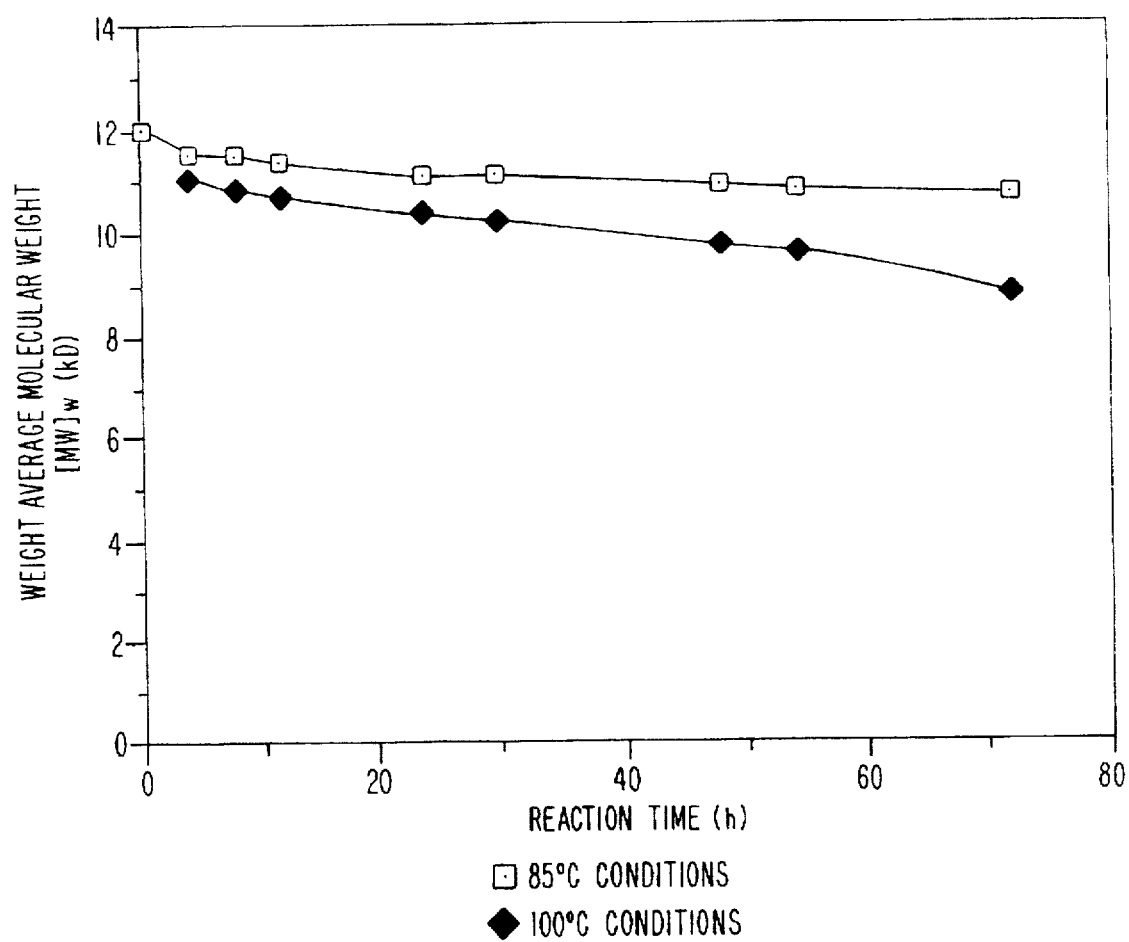
FIG. 1 shows the effect of the solvolysis reaction on the weight average molecular weight |MW|w of the product at 85° C. and 100° C. The weight average molecular weight |MW|w of the product is substantially unchanged, resulting in a substantially unfragmented product.
Figure 2A:
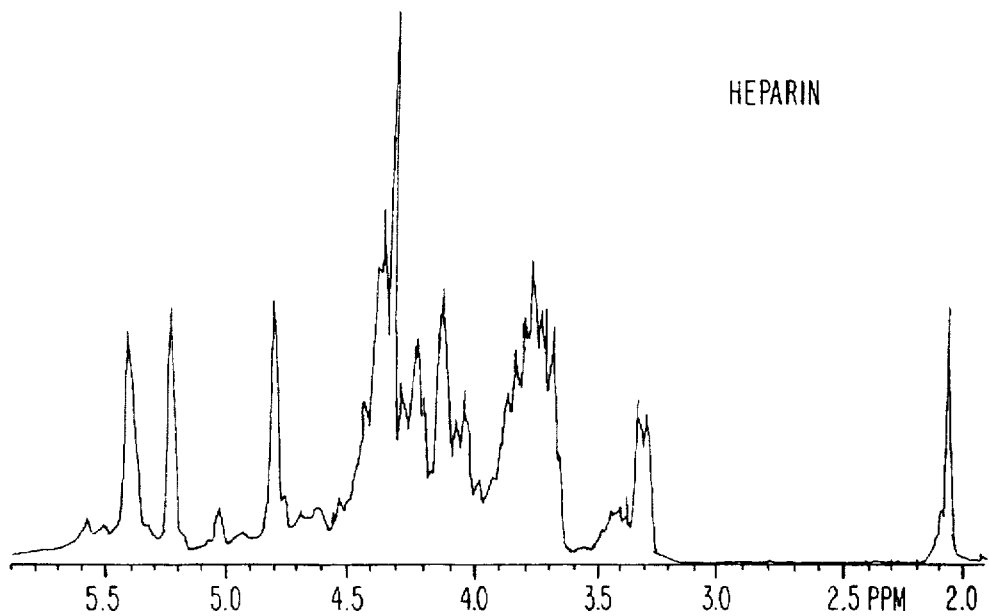
FIG. 2 shows the shifts in H-1 and H-5 for Compositions 1A (i), 2A(i) and 3 (iii), relative to the spectrum of heparin under the same conditions.
Figure 2B:
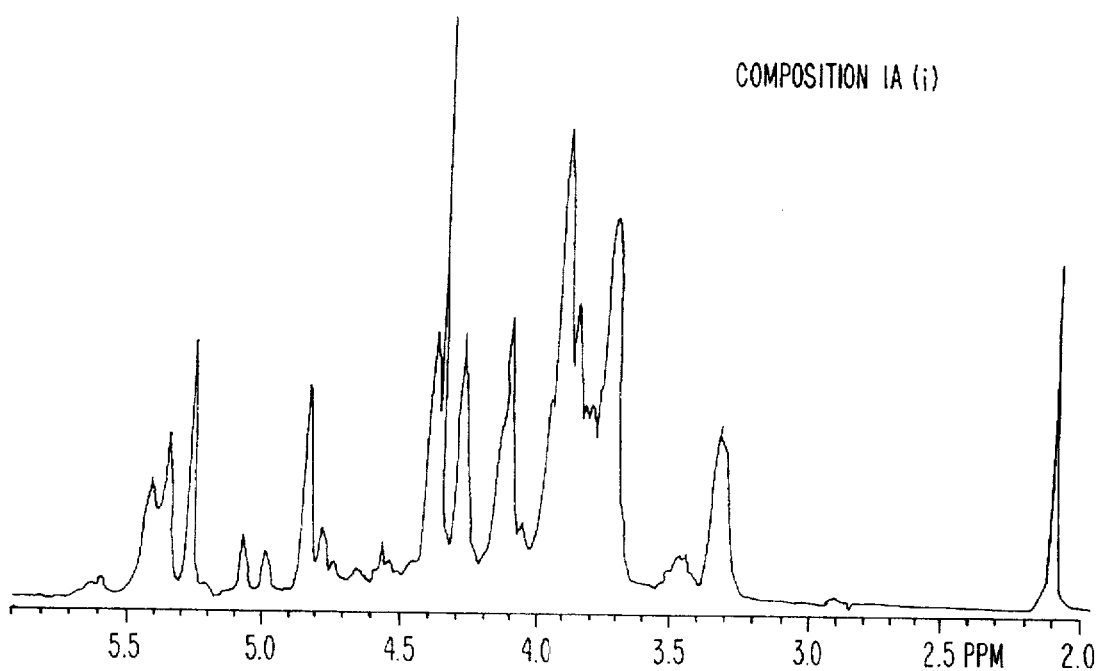
Figure 2C:
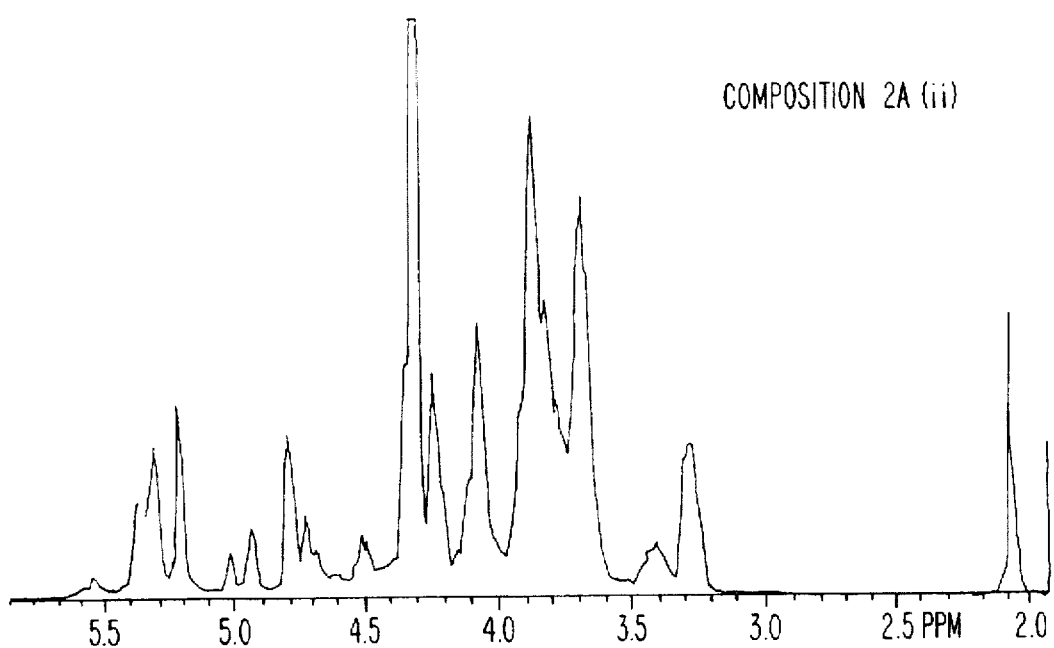
Figure 2D:
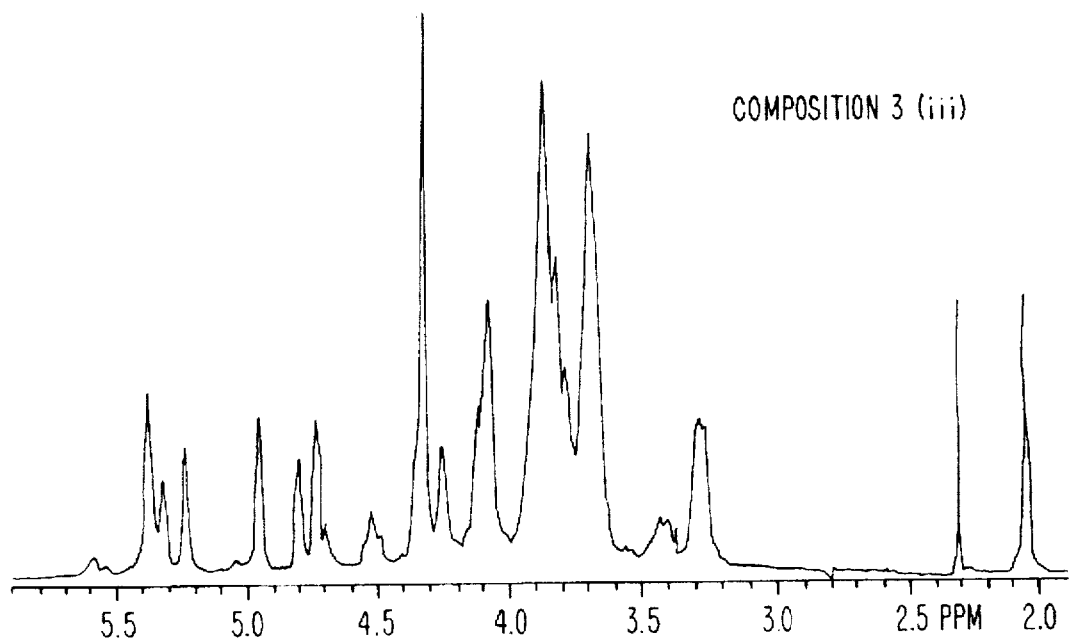

In its most general form, the instant invention relates to compositions and methods of producing the compositions, wherein the compositions consists of substantially unfragmented 6-O desulfated heparin, or 6-O desulfated heparin fragments. The methods permit controlling the per cent of 6-O desulfation such that about <34% of total 6-O positions of disaccharide residues are sulfated, along with partial loss of other O-sulfate groups (up to 67% of total 2-O positions of disaccharide residues are sulfated).

Throughout the specification reference is made to certain scientific publications, patents or patent applications. It is the intent of the Applicants that these references be incorporated in their entirety into the application.

Understanding the invention will be facilitated by a brief discussion of certain of the technical terms used throughout the specification.

By "heparin/heparan sulfate" or "heparin" is meant a preparation obtained from tissues in a manner conventional for the preparation of heparin as an anticoagulant or otherwise synthesized and corresponding to that obtained from tissue. See Conrad, H. E., *Heparin and Related Polysaccharides*, Vol. 56, p. 18 of Annals of N.Y., Academy of Sc., Jun. 7, 1989, incorporated herein by reference. This preparation may include residues of D-glucuronic acid (GlcA), as characteristic of heparan sulfate as well as iduronic acid (IdoA) as characteristic of heparin. However, even though both GlcA and IdoA are present in both, they are present in different proportional amounts. The IdoA/GlcA ratio rises as heparan sulfate becomes more heparin-like. As described in the Background section above, the conversion of D-glucuronic acid to L-iduronic acid is a result of epimerization at the 5 carbon of GlcA residues in a heparan-type intermediate. This sequence of steps involved in such epimerization and conversion is understood in the art. To the extent that full conversion has not been made, heparan sulfate characteristics remain in the preparation. Because the precise nature of the polymeric chains in the preparations of heparin is not generally determined, and varies from preparation to preparation, the term "heparin/heparan sulfate" or "heparin" is intended to cover the range of mixtures encountered. Perhaps the main feature which distinguishes heparan sulfate from heparin is that the latter has anti-coagulant activity.

By heparin fragments, or low molecular weight heparin, is meant heparin that has been treated with any one of a number of reagents and methods that depolymerize heparin with a average molecular weight of 5–30 kd to compositions that have average molecular weights of 2–6.5 kd. Such reagents and methods are known in the art, and examples would include nitrous acid depolymerization, benzylation followed by alkaline depolymerization, peroxidative depolymerization, alkaline treatment, and enzymatic depolymerization with heparinase. See, Hirsh, J. and Levine, M., *Blood* (1992) 79:1–17.

The "heparin/heparan sulfate" or "heparin" preparation can be obtained from a variety of mammalian tissues, including, if desired, human tissue. Generally, porcine or bovine sources are used, and vascularized tissues are preferred. A preferred source of heparin starting material is porcine intestinal mucosa, and preparations labeled "heparin" prepared from this tissue source are commercially available. In general, the heparin starting material is prepared from the selected tissue source by allowing the tissue to undergo autolysis and extracting the tissue with alkali, followed by coagulation of the protein, and then precipitation of the heparin-protein complex from the supernatant by acidification. The complex is recovered by reprecipitation with a polar nonaqueous solvent, such as ethanol or acetone or their mixtures, and the fats are removed by extraction with an organic solvent such as ethanol and proteins by treatment with a proteolytic enzyme, such as trypsin. Suitable procedures for the preparation of the heparin starting material are found, for example, in Charles, A. F., et al., *Biochem J* (1936) 30:1927–1933, and modifications of this basic procedure are also known, such as those disclosed by Coyne, E., in *Chemistry and Biology of Heparin* (1981) Elsevier Publishers, North Holland, N.Y., Lunblad, R. L., et al., eds.

In general, in unmodified heparin 85% of the 6-O positions of GlcN are sulfated and 70% of the 2-O positions of the IdoA are sulfated. It is also understood that the sulfate content and distributions in heparin are somewhat variable. This invention is useful for altering the level and distribution of O-sulfation of the starting heparin/heparan sulfate or other NAC-heparins, to give compositions with reduced anticoagulant activity and other retained activities. "NAC-heparin" or "NAC" refers to a composition of substantially non-anticoagulant, non-fragmented heparin obtained by subjecting commercially available heparin to one or more chemical treatments.

Alkyl- or cyclic-amine salt, wherein alkylamine refers to salt forms of an amine of an alkyl group containing 1 to 6 carbon atoms, and cyclic-amine salts refer to salt forms of those amines where the nitrogen is part of a heterocyclic ring, such as piperidine, morpholine and pyridine, preferably the pyridinium salt form.

It is important to note that the disaccharide analysis of the compositions described and claimed herein are those presented by Guo and Conrad, *Anal. Biochem.* (1988) 168:54–62. Such methods can detect the specific disaccharides within an error of 1–2%. "6-O-desulfated heparin" refers to a composition of substantially non-anticoagulant, non-fragmented heparin wherein the 6-O-position is predominantly desulfated along with partial desulfation at the 2-O-position. "Substantially unfragmented or non-fragmented" refers to compositions wherein the weight average molecular weight |MW|w of the product is substantially unchanged, i.e. the weight average molecular weight |MW|w of the product is 75% or more of the weight average molecular weight |MW|w of the starting material.

In its general form the methods of the instant invention permit controlling the degree of 6-O desulfation of unfragmented heparin, or heparin fragments, to yield compositions of substantially unfragmented 6-O-desulfated heparin, or 6-O-desulfated heparin fragments having a desired per cent of desulfation.

In general, the preferred compositions are defined as:

(i) Compositions 1 and 1 A with <30% of the starting anticoagulant activity, wherein <34% of total 6-O positions and 51–67% of total 2-O positions of disaccharide residues are sulfated. Composition 1A is the product of selective solvolytic O-desulfation of heparin in the presence of a divalent cation, preferably copper. Activities of Composition 1 and 1 A include inhibition of bFGF related activities including angiogenesis and cell proliferation;

(ii) Compositions 2 and 2A possess 5–15% of the starting anticoagulant activity and wherein 12–26% of total 6-O positions and 28–50% of total 2-O positions of disaccharide residues are sulfated. Composition 2A is the product of selective solvolytic O-desulfation of heparin in the presence of a divalent cation, preferably copper. Activities of Composition 2 and 2A include inhibition of bFGF related activities including angiogenesis and cell proliferation; and (iii) Compositions 3 and 3A having <5% anticoagulant activity and wherein <13% of total 6-O positions and 14–28% of total 2-O positions of disaccharide residues are sulfated. Composition 3A is the product of selective solvolytic O-desulfation of heparin in the presence of a divalent cation, preferably copper. Activities of Composition 3 and 3A include selective bFGF-related cell-growth stimulation properties similar to that of heparin.

Briefly the method consists of converting commercially available heparin, preferably Ming Han heparin, 165 U/mg, or heparin fragments, also referred to as low molecular weight heparin (LMW heparin), into a salt form, followed by solvoytic desulfation which causes nearly complete N-desulfation, and most importantly partial O-desulfation. Subsequently, the reaction material is N-resulfated to yield the composition described above. The extent of O-desulfation in the compositions reported in this disclosure depends on the reaction temperature, reaction time, solvolytic solvent composition, solution concentration of heparin salt form, and on the presence of other counter ions in the reaction solution. These reaction parameters are controlled in order to obtain optimal selectively 6-O-desulfated heparin compositions.

Preferably, the method consists of converting commercially available heparin, preferably Ming Han heparin, 165 U/mg, or heparin fragments, also referred to as low molecular weight heparin (LMW heparin), into an alkyl- or cyclic-amine salt, preferably the pyridinium salt form, and then heating a solution of pyridinium heparin in DMSO containing 1–10% water (or methanol) at 60°–110° C. for appropriate lengths of time. The isolated product is almost completely N-desulfated and is reduced in O-sulfate content and particularly in the 6-O-sulfate content. These intermediates are converted into the final products of this invention by subsequent N-resulfation using appropriate conditions as described in the literature (Lloyd et al Biochem. Pharmacol., (1971) 20, 637–648), typically involving treatment with trimethylamine-sulfur trioxide complex (or equivalent reagent) in alkaline aqueous media (pH 9). This achieves substantially complete N-resulfation leading to products that are reduced only in O-sulfate content with respect to the starting heparin.

The heparin derivatives obtained from acid-catalyzed desulfation of heparin are clearly distinct from the derivatives reported here since the order of O-desulfation in acid-catalyzed reactions (2-O-S>6-O-S) is the opposite of the order of O-desulfation in the compositions reported in this disclosure (6-O-S >2-O-S).

The 6-O-sulfate groups in heparin have not been reported to be critical for the anticoagulant activity. However, the compositions characterized in this invention establish that extensive loss of 6-O-sulfate substituents (<34% of total 6-O positions of disaccharide residues are sulfated), in conjunction with partial loss of other O-sulfate groups (up to 67% of total 2-O positions of disaccharide residues are sulfated) does result in substantial reduction of the anticoagulant activity.

Labeled Forms of the Invention Non-Anticoagulant Compositions

The compositions of the invention can be provided with fluorescent, radioisotope, or enzyme labels as desired. Conventional techniques for coupling of label to carbohydrates or related moieties can be used. Such techniques are well established in the art. See, for example, U.S. Pat. No. 4,613,665. The labeled mixtures of the invention may be used to identify sites of disease as well as in competitive immunoassays, and as a means to trace the pharmacokinetics of the compositions in vivo. Suitable radioisotope labels for this purpose include hydrogen$^3$, iodine$^{131}$, indium$^{111}$, technetium$^{99}$, and phosphorus$^{32}$. Suitable enzymic labels include alkaline phosphatase, glucose-6-phosphate-dehydrogenase, and horseradish peroxidase. Particularly preferred fluorescent labels include fluorescein and dansyl. A wide variety of labels of all three types is known in the art. administration and Use The non-anticoagulant heparin compositions of the instant invention are useful in therapeutic applications for treating or preventing a variety of diseases including restenosis, cancer, angiogenesis, shock, ischemia reperfusion injury, inflammation, cardiovascular diseases and diseases caused or exacerbated by platelet aggregation, heparanase or angiogenic activity. The instant 6-O desulfated heparin compositions, because of their anti-angiogenic activity, will be preferably applied for the beneficial treatment of angiogenic based diseases. One such class of diseases is retinopathies. A member of this class is diabetic retinopathy that will be favorably treated by the compositions of the instant invention. Another application of the composition of the instant invention is the treatment or prevention of cancer, particularly metastatic and invasive cancers, preferably by inhibiting angiogenesis which facilitates or is required for the growth and spread of cancer throughout a patients body.

Yet another application of the composition of the instant invention is the treatment or prevention of shock, including for example, hypovolemic shock and septic shock. The mechanism of many diseases such as hypovolemic shock are complex and the result of multiple causes. Accordingly, "treating" as used herein indicates a methodology which interferes with one or more causes or events and thereby has a beneficial impact on the individual being treated. It is understood that to "treat" hypovolemic shock includes preventing, delaying or in some way reducing the onset of symptoms without perhaps actually removing the cause for shock completely. Accordingly, treatment with the present invention compositions may extend life and/or improve its quality even though the individual being treated ultimately succumbs to shock.

The invention compositions are also applicable to the prevention of such shock in patients that are at a high risk of developing the disease. For instance, certain conditions carry a high risk of developing hypovolemic shock including hemorrhage, trauma, burns, polyuria, vomiting, and diarrhea. See, *Circulatory Shock*, (1992) 91:7. Thus, a patient hospitalized for one of these conditions may be administered the compositions of the invention to prevent the development of hypovolemic shock. Consequently, while reference throughout the patent application is made to methods of treating hypovolemic shock it will be understood by the skilled practitioner of this art that such terminology encompasses preventing shock as well.

It should be noted that the preferred therapeutic compositions consist of fragments of 1, 1A, 2, 2A, 3 and 3A. Because of their reduced size such fragments exhibit favored bioavailability and pharmacokinetic properties. See, Hirsh, J. and Levine, M., *Blood* (1992) 79:1–17.

Administration of either substantially unfragmented 6-O desulfated heparin, or 6-O desulfated heparin fragments is typically by routes appropriate for glycosaminoglycan compositions, and generally includes systemic administration, such as by injection.

Particularly preferred is intravenous injection, as continuous injection over long time periods can be easily continued. Also preferred are introduction into the vascular system through intraluminal administration or by adventitial administration using osmotic pumps or implants. Typical implants contain biodegradable materials such as collagen, polylactate, polylactate/poly-glycoside mixtures, and the like. These may be formulated as patches or beads. Typical dosage ranges are in the range of 0.1–10 mg/kg/hr on a constant basis over a period of 5–30, preferably 7–14, days. Particularly preferred dosage is about 0.3 mg/kg/hr, or, for a 70 kg adult, 21 mg/hr or about 500 mg/day.

Other modes of administration are less preferred but may be more convenient. Injection subcutaneously at a lower dose or administered orally at a slightly higher dose than intravenous injection, or by transmembrane or transdermal or other topical administration for localized injury may also be effective. Localized administration through a continuous release device, such as a supporting matrix, perhaps included in a vascular graft material, is particularly useful where the location of the trauma is accessible.

Formulations suitable for the foregoing modes of administration are known in the art, and a suitable compendium of formulations is found in *Remington's Pharmaceutical Sciences*, Mack Publishing Company, Easton, Pa., latest edition.

The compositions of the invention may also be labeled using typical methods such as radiolabeling, fluorescent labeling, chromophores or enzymes, and used to assay the amount of such compositions in a biological sample following its administration. Suitable protocols for competitive assays of analytes in biological samples are well known in the art, and generally involve treatment of the sample, in admixture with the labeled competitor, with a specific binding partner which is reactive with the analyte such as, typically, an immunoglobulin or fragment thereof. The antibodies prepared according to the invention, as described below, are useful for this purpose. The binding of analyte and competitor to the antibody can be measured by removing the bound complex and assaying either the complex or the supernatant for the label. The separation can be made more facile by preliminary conjugation of the specific binding partner to a solid support. Such techniques are well known in the art, and the protocols available for such competitive assays are too numerous and too well known to be set forth in detail here.

Antibodies may be prepared to 6-O desulfated heparin, or 6-O desulfated heparin fragments by direct injection into an appropriate animal host, or by coupling the compositions to suitable carriers and administering the coupled materials to mammalian or other vertebrate subjects in standard immunization protocols with proper inclusion of adjuvants. Suitable immunogenic carriers include, for example, Keyhole Limpet Hemocyanin (KLH), tetanus toxoid, various serum albumins such as bovine serum albumin (BSA) and certain viral proteins such as rotaviral VP6 protein. These coupled materials are then administered in repeated injections to subjects such as rabbits, rats or mice and antibody titers monitored by standard immunoassay techniques. The resulting antisera may be used per se or the antibody-secreting cells generated by the immunization may be immortalized using standard techniques and used as a source of monoclonal preparations which are immunoreactive with 6-O desulfated heparin, or 6-O desulfated heparin fragments.

Methods to conjugate 6-O desulfated heparin, or 6-O desulfated heparin fragments to carriers are known in the art. The compositions may be linked to the carrier by, for example, homo- or heterobifunctional linkers such as those marketed by Pierce Chemical Company, Rockford, Ill. Certain covalent linkers are described in U.S. Pat. No. 4,954,637.

Murine or human monoclonal preparations can be obtained by In vivo or in vitro immortalization of peripheral blood lymphocytes or spleen cells of animals using methods well known in the art, such as fusion with immortalizing cells as described by Kohler and Millstein *Nature* (1975) 256:495; and Fendly, et al., *Hybridoma* (1987) 6:359. In vitro techniques are generally described by Luben, R. and Mohler, M., *Molecular Immunology* (1980) 17:635; Reading, C. *Methods in Enzymology* (1986) 121:18 (Part 1); or Voss, B., *Methods in Enzymology* (1986) 121:27. Recombinant and/or humanized antibody may also be generated using methods known in the art.

Properties of 6-O Desulfated Heparin, or 6-O Desulfated Heparin Fragments

As discussed above, heparin and non-anticoagulant heparins are biologically active. Certain assays were conducted to determine the biological properties of the instant invention compositions, and compare these to the properties of heparin or known non-anticoagulant heparins. A particularly noteworthy property of the 6-O desulfated heparin is its low in vivo toxicity. The properties studied and the assays used are described in detail in the Examples below.

The following examples are intended to illustrate but not to limit the invention. For example, those skilled in the art would know that there are materials and methods that can be substituted for those described below, and still come within the scope of what is taught in the Examples.

EXAMPLE 1

Production of 6-O desulfated heparin

Figure 3A:
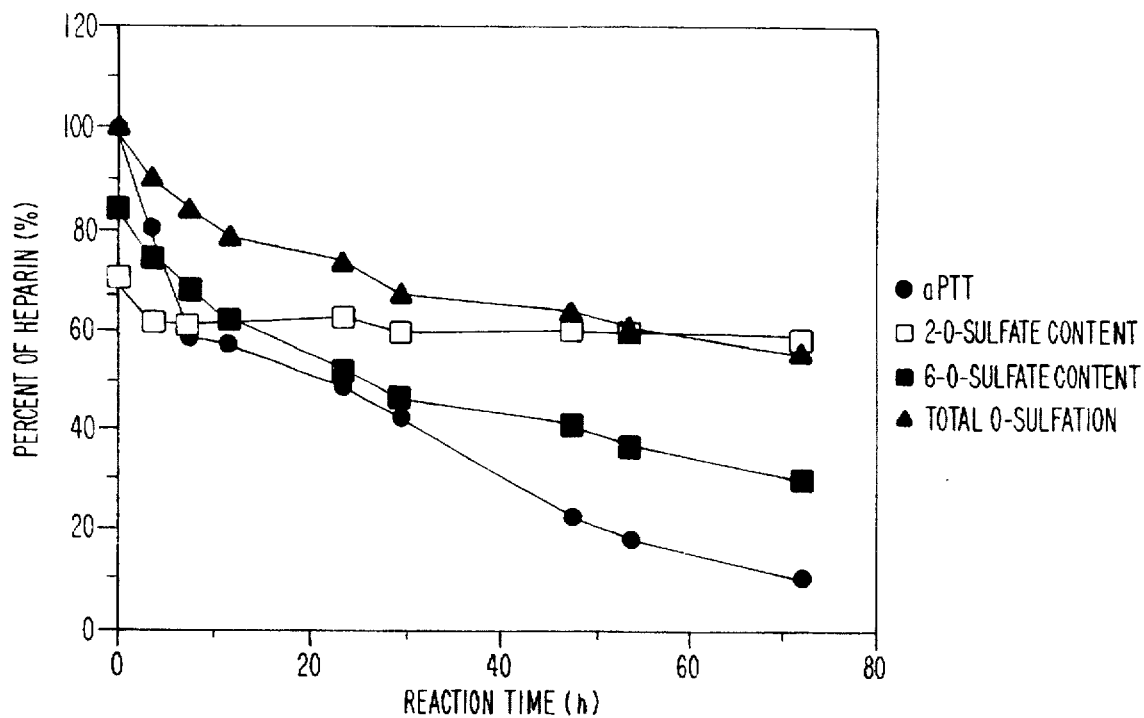
FIG. 3A shows the effect of solvolytic O-desulfation, the data being expressed in terms of percent aPTT, percent of disaccharides containing 2-O-sulfated IdoA and percent of disaccharides containing 6-O-sulfated GlcN for the 70° C. solvolysis time course reactions in order to contrast-the relative importance of specific O-sulfate groups. 6-O-desulfation occurs selectively, with virtually no concomitant loss of 2-O-sulfates under these reaction conditions. The anticoagulant activity declined fairly quickly, over the reaction time course, to about 50% of the starting heparin and declined to about 10% anticoagulant activity, following the loss of 6-O sulfate groups.

Table 1 lists the reaction conditions used to synthesize Compositions 1, 1A 2, 2A, 3 and 3A. A detailed examination of the effects of reaction temperature and time on the composition and anticoagulant activity of products from a solvolysis time course was performed at 70 and 100° C., both in the absence of copper (FIGS. 3A and 3B, respectively), and in the presence of copper (FIGS. 4A and 4B, respectively). All other reaction parameters were kept constant in order to allow appropriate comparison of the results. In general, 2.0 g of pyridinium heparin was dissolved in 10 ml of water and then diluted with 90 ml of DMSO. The solution was heated in a temperature controlled oil bath with constant stirring. Aliquots (10 ml) were withdrawn at indicated time intervals, transferred to a tube containing 5 ml of 5% sodium bicarbonate and cooled. All of the aliquots were dialyzed twice against 10 volumes of 0.1M sodium acetate solution for 12 h, and then exhaustively against distilled water.

N-Resulfation The reaction conditions to achieve mild and selective N- sulfation of free amine functionalities in heparin derivatives were similar to those reported by Lloyd et al (Biochem. Pharmacol., (1971) 20, 637–648). The heparin derivative or solvolysis product was treated with excess (3–5 molar equivalents) TMA/$SO_3$ or pyridine/$SO_3$ in 0.1M aqueous sodium carbonate at 50°–60° C. for 24 h. The excess sulfation reagent is typically added in three aliquots over the reaction time course to ensure complete reaction. After reaction, the solutions were dialyzed exhaustively against distilled water, filtered and lyophilized.

In general, the compositions of interest are defined as;

(i) Compositions 1 and 1 A with <30% of the starting anticoagulant activity, wherein <34% of total 6-O positions and 51–67% of total 2-O positions of disaccharide residues are sulfated. Composition 1A is the product of selective solvolytic O-desulfation of heparin in the presence of a divalent cation, preferably copper. Activities of Composition 1 and 1A include inhibition of bFGF related activities including angiogenesis and cell proliferation;

(ii) Compositions 2 and 2A possess 5–15% of the starting anticoagulant activity and wherein 12–26% of total 6-O positions and 28–50% of total 2-O positions of disaccharide residues are sulfated. Composition 2A is the product of selective solvolytic O-desulfation of heparin in the presence of a divalent cation, preferably copper. Activities of Composition 2 and 2A include inhibition of bFGF related activities including angiogenesis and cell proliferation; and (iii) Compositions 3 and 3A having <5% anticoagulant activity and wherein <13% of total 6-O positions and 14–28% of total 2-O positions of disaccharide residues are sulfated. Composition 3A is the product of selective solvolytic O-desulfation of heparin in the presence of a divalent cation, preferably copper. Activities of Composition 3 and 3A include selective bFGF-related cell-growth stimulation properties similar to that of heparin.

Structural characterization: All of the samples isolated from the reaction time courses were analyzed using a variety of methods. Analysis was typically done on the N-resulfated products. FIG. 1 shows the effect of the solvolysis reaction on the weight average molecular weight [MW]w of the product at 85° C. and 100° C. The weight average molecular weight [MW]w of the product is substantially unchanged, resulting in a substantially unfragmented product.

$^1$H-nmr spectroscopy: 300 MHz 1 H-nmr characterization of partially O-desulfated products was most effective when performed on the N-resulfated products on solutions in $D_2O$ adjusted to pH>9 by the addition of $Na_2CO_3$. Two aspects of these spectra that are most informative are the shifts in IdoA H-1 and IdoA H-5 as a result of loss of 2-O-sulfate from IdoA. These resonances are relatively insensitive to the loss of 6-O-sulfate. The shifts in 1H-1 and 1H-5 are indicated in FIG. 2, for Composition 3 which has lost >90% GlcN 6-O-sulfate and <20% IdoA 2-O-sulfate, relative to the spectrum of heparin under the same conditions.

Disaccharide composition: Compositional analysis of the products was accomplished using methods for disaccharide analysis that have been described by (Guo, Y., and Conrad, H. E., *Anal. Biochem.* (1989) 176:96, and Guo, Y., and Conrad, H. E., *Anal. Biochem.* (1988) 168:54). Briefly, the sample was treated with hydrazine to totally de-N-acetylate the material, which was then sequentially treated with nitrous acid at pH 1.5 and 4.0. These conditions provided complete conversion of heparin like polymers into constituent disaccharides in which the GlcN residue has been converted into the respective anhydromannose residue. Reduction of the disaccharide mixture with $NaB^3H_4$ provided labelled disaccharides appropriate for the complete analysis of constituents of the parent polymer.

Reverse phase ion-pairing HPLC (Guo, Y., and Conrad, H. E., *Anal. Biochem.* (1989) 176:96) was used to quantitate the mono (ISM, IMS and GMS) and disulfated disaccharides (ISMS and $GMS_2$) in the sample. Non-sulfated disaccharides are also present in these products and were quantitated using paper electrophoresis (Shively, J. E. and Conrad, H. E. *Biochem.* (1976) 15:3943). Relative amounts of non-, mono- and disulfated disaccharides were calculated from the HPLC and paper electrophoresis data.

TABLE 1

| Composition | Pyridinium heparin/$CuSO_4$ (gm) | APTT (%) | Temp (°C.) | Time (hrs) | Yield (±5%) |
|---|---|---|---|---|---|
| 1 (i) | 2/— | 23 | 70 | 48 | 80 |
| (ii) | 2/— | 27.4 | 85 | 8 | 80 |
| 1A (i) | 2/0.26 | 27 | 80 | 30 | 80 |
| (ii) | 2/0.25 | 30 | 95 | 24 | 75 |
| 2 (i) | 2/— | 11 | 70 | 72 | 80 |
| (ii) | 2/— | 13.3 | 85 | 12 | 80 |
| (iii) | 2/— | 6.9 | 100 | 4 | 80 |
| 2A (i) | 2/0.26 | 7 | 80 | 30 | 80 |
| (ii) | 2/0.26 | 5.2 | 90 | 30 | 80 |
| (iii) | 0.25/0.032 | 11 | 95 | 24 | 83 |
| 3 (i) | 2/— | 1.6 | 90 | 30 | 80 |
| (ii) | 2/— | 5 | 95 | 30 | 85 |
| (iii) | 0.25/— | 1 | 95 | 30 | 85 |
| 3A (i) | 2/0.26 | 3.4 | 90 | 30 | 80 |
| (ii) | 2/0.26 | 1.2 | 95 | 30 | 85 |

Anticoagulant activity: Activated partial thromboplastin time (APTT) was determined using a citrated plasma-based clotting assay based on the activation of the intrinsic system through factor XII using either a chemical or particulate activator. The APTT assay is described in depth in J. M. Walenga et al., "In Vitro Evaluation Of Heparin Fractions: Old vs. New Methods" *CRC Critical Reviews in Clinical Laboratory Systems* 22 at 362 which is incorporated herein by reference.

The APTT values were calculated as a percent of heparin, the value for heparin being 100%. FIG. 3A shows the effect of solvolytic O-desulfation, the data being expressed in terms of percent aPTT, percent 2-O-sulfated disaccharide content and percent 6-O-sulfated disaccharide content for the 70° C. solvolysis time course reactions in order to contrast the relative importance of specific O-sulfate groups. The trend seen here supports the observation that 6-O-desulfation occurs selectively, with virtually no concomitant loss of 2-O-sulfates. The anticoagulant activity declined fairly quickly, over the reaction time course, to about 50% of the starting heparin and declined to about 10% more gradually, roughly following the trend of loss of 6-O sulfate groups.

The anticoagulant activity of product from the solvolysis reaction carried out according to Example 1 at 100° C. (FIG. 3B) declined very rapidly over time to <10% after 4 h. By 12 h the activity was <1% of the original activity despite having ~40% of the original 2-O-sulfate content in the form of ISM disaccharide units.

Effect of Copper on the solvolysis reaction: The effect of solvolytic O-desulfation time course on the percent aPTT, percent 2-O-sulfated disaccharide content and percent 6-O-sulfated disaccharide content for the solvolysis reaction in the presence of copper (II) sulfate at 70° C. and 100° C. are presented graphically in FIGS. 4A and 4B respectively.

In the 70° C.+Cu(II) time course (FIG. 4A) the anticoagulant activity was markedly affected by the presence of Cu(II) reaching only 30% of starting activity after 72 h. The retention of anticoagulant activity at later time points may be due to the fact that ISMS was elevated by about 5%, or to the fact that $GMS_2$ was not totally lost as it was when Cu(II) was not present. The trend seen in FIG. 4A supports the observation that 6-O-desulfation occurs selectively, with virtually no concomitant loss of 2-O-sulfates.

The 100° C. time course reaction in the presence of Cu(II) showed only minor variation in the disaccharide profile (FIG. 4B) relative to solvolysis in the absence of Cu(II). The anticoagulant activity profile showed an overall slower loss of activity, possibly correlated to the slower conversion of ISMS and ISM rather than any effect related to $GMS_2$.

A solvolytic time course reaction at 85° C. in the presence of Cu(II) was performed, and initial data supported the trend expected based on the 70 and 100° C. reactions in the presence of Cu(II).

Figure 5:
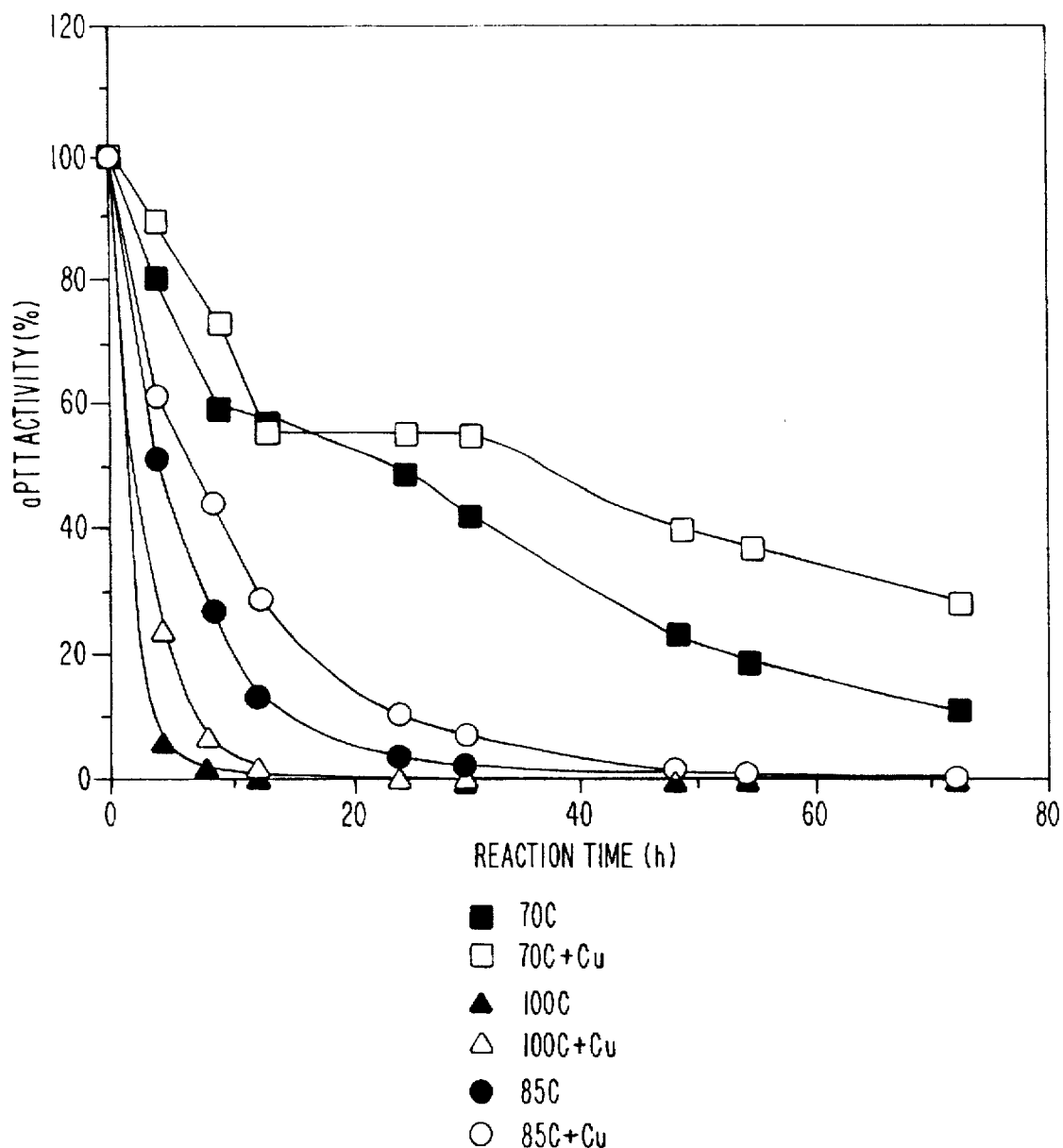
FIG. 5 shows the anticoagulant activity of products from time course reactions at 70, 85 and 100° C. solvolysis reaction.The reduction in anti-coagulant activity was dramatically affected by reaction temperature.

The anticoagulant activity of products from all of the time course reactions at 70, 85 and 100° C. are presented graphically in FIG. 5. Clearly, reduction in anticoagulant activity was dramatically affected by reaction temperature. The presence of Cu(II) ion had a protective effect on aPTT which was more effective at lower temperatures.

Figure 3B:
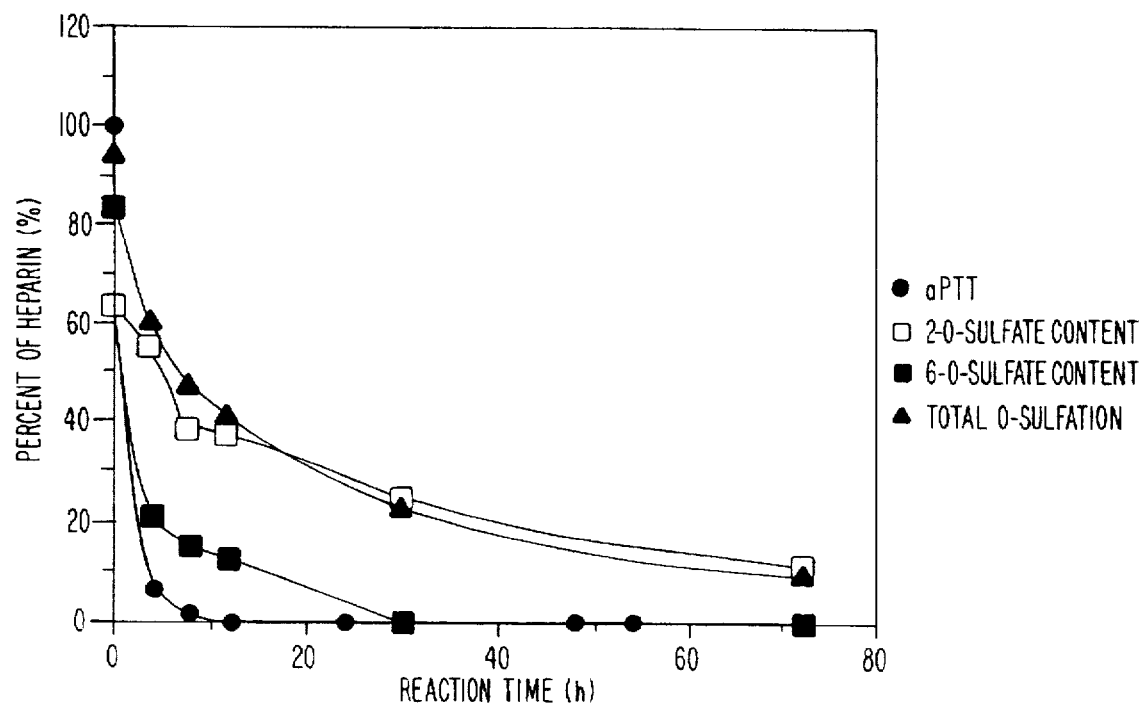
FIG. 3B shows the effect of solvolytic O-desulfation, the data being expressed in terms of percent aPTT, percent of disaccharides containing 2-O-sulfated IdoA, and percent of disaccharides containing 6-O-sulfated GlcN for the 100° C. solvolysis time course reactions in order to contrast the relative importance of specific O-sulfate groups. The anticoagulant activity of product compositions declined very rapidly to <10% after 4h.
Figure 4A:
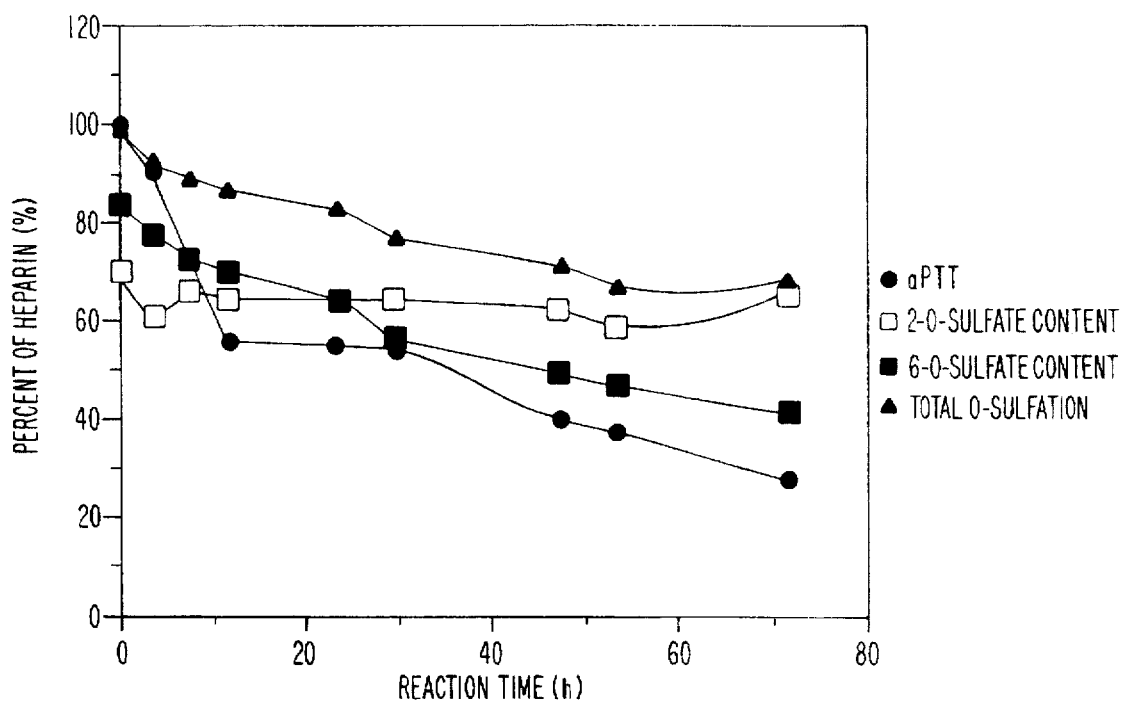
FIG. 4A shows the effect of solvolytic O-desulfation, the data being expressed in terms of percent aPTT, percent of disaccharides containing 2-O-sulfated IdoA and percent of disaccharides containing 6-O-sulfated GlCN for the solvolysis reaction in the presence of copper (II) sulfate at 70° C.+Cu(II) time course. The anticoagulant activity was markedly affected by the presence of Cu(II) reaching only 30% of starting activity after 72h.
Figure 4B:
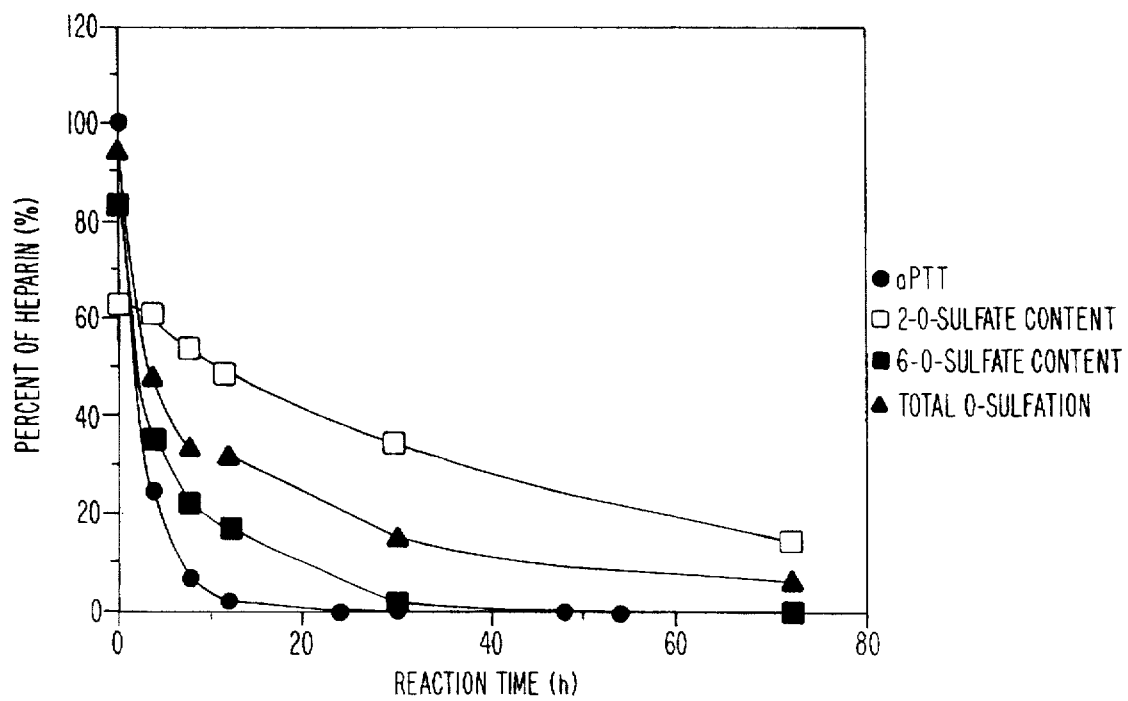
FIG. 4B shows the effect of solvolytic O-desulfation, the data being expressed in terms of percent aPTT, percent of disaccharides containing 2-O-sulfated IdoA and percent of disaccharides containing 6-O-sulfated GlcN for the solvolysis reaction in the presence of copper (II) sulfate at 100° C.+Cu(II) time course. The 100° C. time course reaction in the presence of Cu(II) showed only minor variation in the disaccharide profile relative to solvolysis in the absence of Cu(II). The profile showed an overall slower loss of anticoagulant activity, possibly correlated to the slower conversion of ISMS and ISM rather than any effect related to $GMS_2$.

It can be concluded from FIG. 3B that solvolysis at 100° C. results in a dramatic increase in the rate of 6-O-sulfate loss accompanied by some 2-O-desulfation. Compositions with <25% of 6-O-sulfate content and >90% of 2-O-sulfate content were obtained at 4 h reaction time and had <10% of the anticoagulant activity of the starting heparin. Similar compositions were obtained after 8 h when the solvolysis, as described in above, was performed in the presence of Cu(II) (FIG. 4B). These results also indicate that significant loss of 2-O-sulfate is not required for significant reduction in anticoagulant activity.

EXAMPLE 2

Anti-Angiogenic Activity

Compounds that stimulate or inhibit angiogenesis can be identified using several assays known in the art. Compositions 2A (i) and 3 (iii) produced as described in Example 1 above, were tested using the chicken chorioallantoic membrane (CAM) assay. The assay was performed as described by Castellot et. al., *J. of Cellular Physiology* (1986) 127: 323–329, with the exception that samples were evaluated for their efficacy to inhibit neovascularization. Agarose pellets containing 50 µg of hydrocortisone, or hydrocortisone plus different amounts of 6-O desulfated heparin were incubated on the CAM for 3–4 days before scoring the results.

Table 2 shows the results. It is apparent that the Composition 2A(i) exhibits angiostatic activity. The more extensively O-desulfated product, Composition 3 (iii) showed weaker activity. Angiostatic activity is defined as a partial clearing or an avascular zone around the pellet. In all cases, pellets at each heparinoid concentration contained 50 µg of hydrocortisone.

The number in parenthesis in Table 2 is the per cent of the total embryos scored that exhibited no effect, a partial clearing, or an avascular zone. For example, 50 µg/ml of Composition 2A (i) had no effect on 5 embryos and a partial clearing on 8 embryos. Thus, under these conditions 38.5% of the embryos showed no effect and 61.5% exhibited a partial clearing.

TABLE 2

| Chick Chorioallantoic Membrane Bioassay | | | | |
|---|---|---|---|---|
| Composition | Conc (µg/ml) | No Effect (%) | Partial Clearing (%) | Avascular Zone (%) |
| 2A (i) | 50 | 5 (38.5) | 8 (61.5) | 0 (0) |
|  | 25 | 3 (21.4) | 11 (78.6) | 0 (0) |
|  | 12.5 | 10 (66.7) | 5 (33.3) | 0 (0) |
|  | 6.25 | 6 (40) | 8 (53.3) | 1 (6.7) |
| 3 (iii) | 50 | 10 (83.3) | 2 (16.7) | 0 (0) |
|  | 25 | 8 (53.3) | 7 (46.7) | 0 (0) |
|  | 12.5 | 15 (88.2) | 2 (11.8) | 0 (0) |
|  | 6.25 | 12 (85.7) | 2 (14.3) | 0 (0) |
| Heparin | 50 | 2 (13.3) | 7 (46.7) | 6 (40) |
|  | 12.5 | 2 (14.3) | 11 (78.6) | 1 (7.1) |
| Control | 0 | 13 (81.3) | 3 (18.7) | 0 (0) |

EXAMPLE 3

Heparanase Inhibitory Activities of Compositions 2A (iii) and 3 (ii) Compositions 2A (iii) and 3 (ii) were tested for heparanase inhibitory activity using heparanase from a rat hepatoma cell line. The cell line is described by Gerschenson, et al., *Science* (1970) 170: 859–861.

The procedures for isolating heparanase from hepatoma cells, and the methods for assaying the activity of the enzyme are known by those skilled in the art. The following procedures and materials were used.

Confluent rat hepatoma cell cultures were grown in standard cell culture flasks, and washed 3 times with 10 ml of a 50 mM Hepes solution containing 0.25M sucrose and 0.14M NaCl, pH 7.4. Next, 1 ml of a 50 mM MES buffer pH 5.2, containing 0.14M NaCl, 6 mM sodium azide, and certain protease inhibitors was added and the cells removed from the flask using a disposable cell scraper. The following protease inhibitors were present in the MES buffer: 0.2 µg/ml aprotinin, 0.5 µg/ml leupeptin,100 µg/ml soybean trypsin inhibitor,1 mM PMSF, 2 mM EDTA (sodium salt), and 15mM D-saccharic acid 1,4 lactone (exoglucuronidase inhibitor).

The cells were added to a 7 ml Dounce homogenizer, freezed/thawed 3 times in an ethanol/dry ice bath, and homogenized with 15 strokes using a tight pestle. The resulting cell lysates were placed in a 2 ml centrifuge tube and centrifuged at 4° C. for 30 minutes at 16,000×g. The supernatant was removed, and the protein concentration in the supernatant determined using the Macro BCA protein assay. BSA was used as a standard.

Heparanase activity was quantified by measuring soluble N-3H-acetylated pancreas heparan sulfate fragments derived from uncleaved N-3H-acetylated pancreas heparan sulfate by cetylpyridinium chloride (CPC) precipitation. N-$^3$H-acetylated pancreas heparan sulfate had a weight average molecular weight, or Mw, of about 12,000. The following procedures were used.

Rat hepatoma cell supernatant, isolated as described above, containing 10 µg of protein was brought up to 30 µl with 50 mM MES buffer pH 5.2 containing 0.14M NaCl, 6 mM sodium azide and the protease inhibitors described above, and added to siliconized 1.5 ml microcentrifuge tubes. Next, $^3$H-acetylated pancreas heparan sulfate (93 ng, 30,000 cpm) in 10 µl of 200 mM MES buffer pH 5.2 containing 0.14M NaCl was added to tubes containing the rat hepatoma cell supernatant. 10 µl of distilled water containing various concentrations of Compositions 2A (iii) and 3(ii) was added. The assay was run in triplicate for each inhibitor concentration. Three "0" time points were run as controls in which no inhibitor was added. It was previously shown that the highest concentration of inhibitor does not affect precipitation of the intact radiolabeled heparan sulfate substrate.

The enzyme substrate inhibitor mixture was spun in a microcentrifuge, after which the tubes were incubated at 37° C. for 30 minutes. The "0" time points were maintained on ice. After the appropriate time, the reaction was stopped by adding to the reaction tubes the following:

1) 150 µl of an aqueous heparin solution (0.33 mg/ml)
2) 200 µl of 100 mM sodium acetate pH 5.5
3) 100 µl of CPC (0.6% in water)

Next, the tubes were vortexed, incubated for 60 minutes at room temperature, and then centrifuged for 10 minutes at 4,000×g in a 5415C Eppendorf centrifuge. The supernatant was removed and assayed for $^3$H by liquid scintillation counting.

Composition 2A (iii) was shown to be approximately as effective as heparin in inhibiting heparanase from rat hepatocytes. A relative IC$_{50}$ of 1.0±0.1 was obtained in duplicate experiments. A slightly more desulfated analog, Composition 3 (ii), had a slightly lower activity, with a relative IC$_{50}$ of 0.9±0.1. Thus, these results establish that the 6-O desulfated heparin composition of the instant invention are heparanase inhibitor.

EXAMPLE 4

Activity of Compositions 1A, 2A, 3 and 3A in bFGF Binding Assay

The interaction of select products from a time course reaction were evaluated for ability to interact with bFGF in an in-vitro cell based assay as described by Ishihara, M., et al., *Analytical Biochemistry* (1992) 202:310 and Ishihara, M., et al., *J. Biol. Chem.* (1993) 268:4675. Table 3 contains data supporting the bFGF-related properties of Compositions 1A (i) and (ii), 2A (i), (ii) and (iii), 3 (i), (ii) and (iii) and 3A (ii). It is important to note that Compositions 1A and 2A inhibit and stimulate similar to heparin, while Compositions 3 and 3A inhibits less, but retains stimulatory properties.

These bFGF-related properties are supported by additional data obtained from a study of oligosaccharides derived from selectively 6-O-desulfated heparin derivatives. The size and structure defined oligosaccharides were prepared after hydrazinolysis of Composition 1A (ii) to N-deacetylate the polymer. The sample was then treated with nitrous acid at pH 4 for 10 min. to yield a mixture of fragments with N-sulfated glucosamine residues. The reaction mixture was then incubated at pH 3 to accomplish further depolymerization. The resulting oligosaccharides were reduced in alkaline conditions using sodium borohydride.

Oligosaccharides were separated by gel filtration chromatography on Bio-Gel P-10 (BioRad) column (3×200 cm). The column was equilibrated in and eluted with 0.5M ammonium bicarbonate, and fractions assayed for uronic acids by the carbazole method. The pools of oligosaccharides were then rechromatographed using a P-10 column to further ensure the size homogeneity. The respective oligosaccharides were then fractionated on a Q-sepharose (Pharmacia) column (1×5 cm) equilibrated with 0.2M sodium chloride in 10 mM Tris, pH 7.3. After loading, unbound oligosaccharides were washed off with 20 mL of buffer, and the remaining oligosaccharides were washed off with a linear gradient of sodium chloride (0.2 to 2.0M NaCl). Each oligosaccharide pool generated was divided into six different subpools differing in affinity for Q-sepharose, and the subpools were eluted with the highest concentrations of NaCl were then dialyzed against distilled water using 1000 MWCO dialysis membrane (Spectrum) Carbazole assay was used to monitor all column fractions for material. Analysis of the composition of the respective oligosaccharide pools was accomplished using the disaccharide analysis described previously.

Figure 6A:
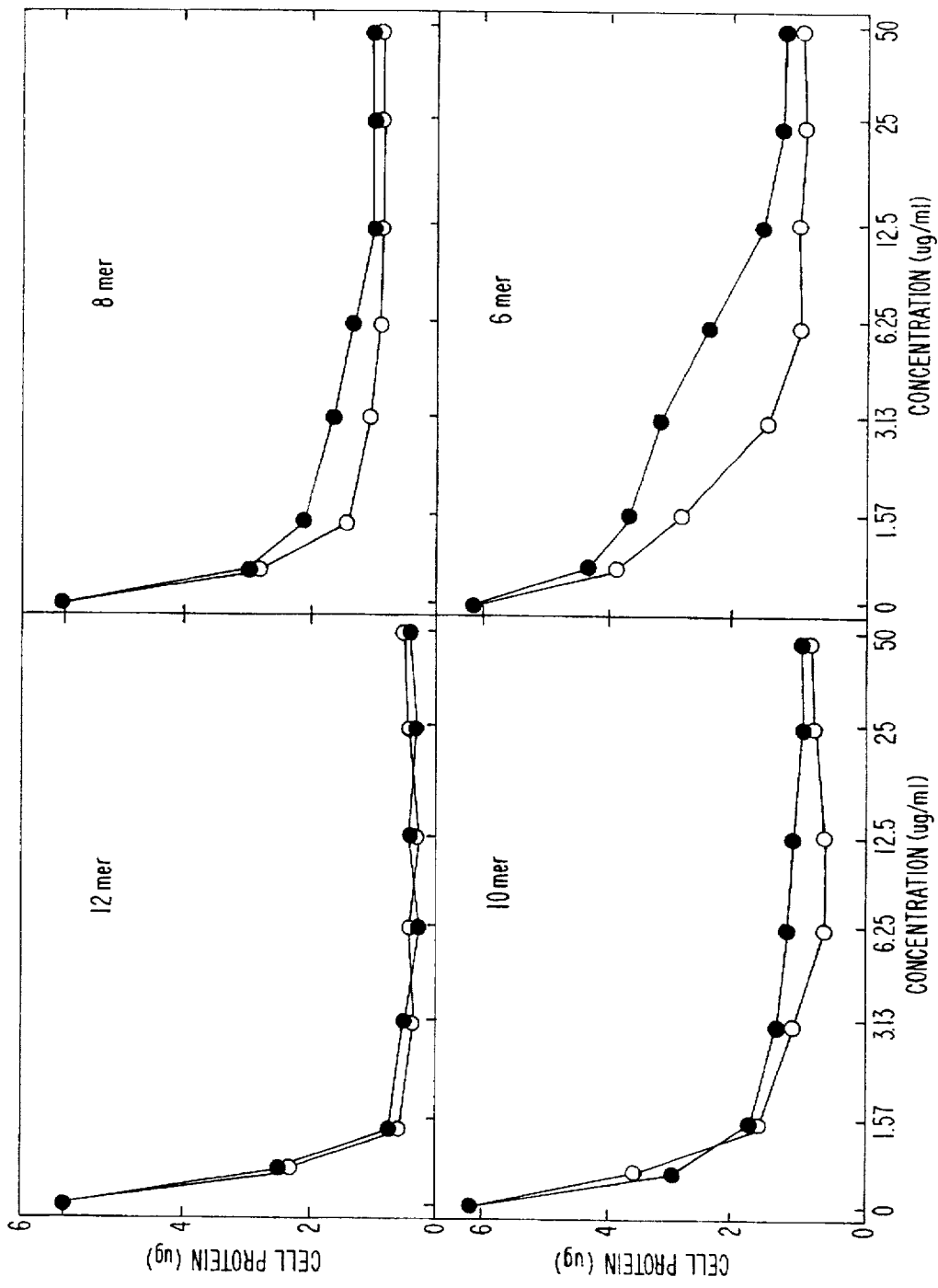
FIG. 6A shows the results of the effect of Composition 1A (ii) in the assay to determine bFGF binding to RO-12 UC cells. The hexa, octa, deca and dodecamers from Composition 1A (ii) inhibited bFGF binding to RO-12 UC cells about as well as heparin oligosaccharides.
Figure 6B:
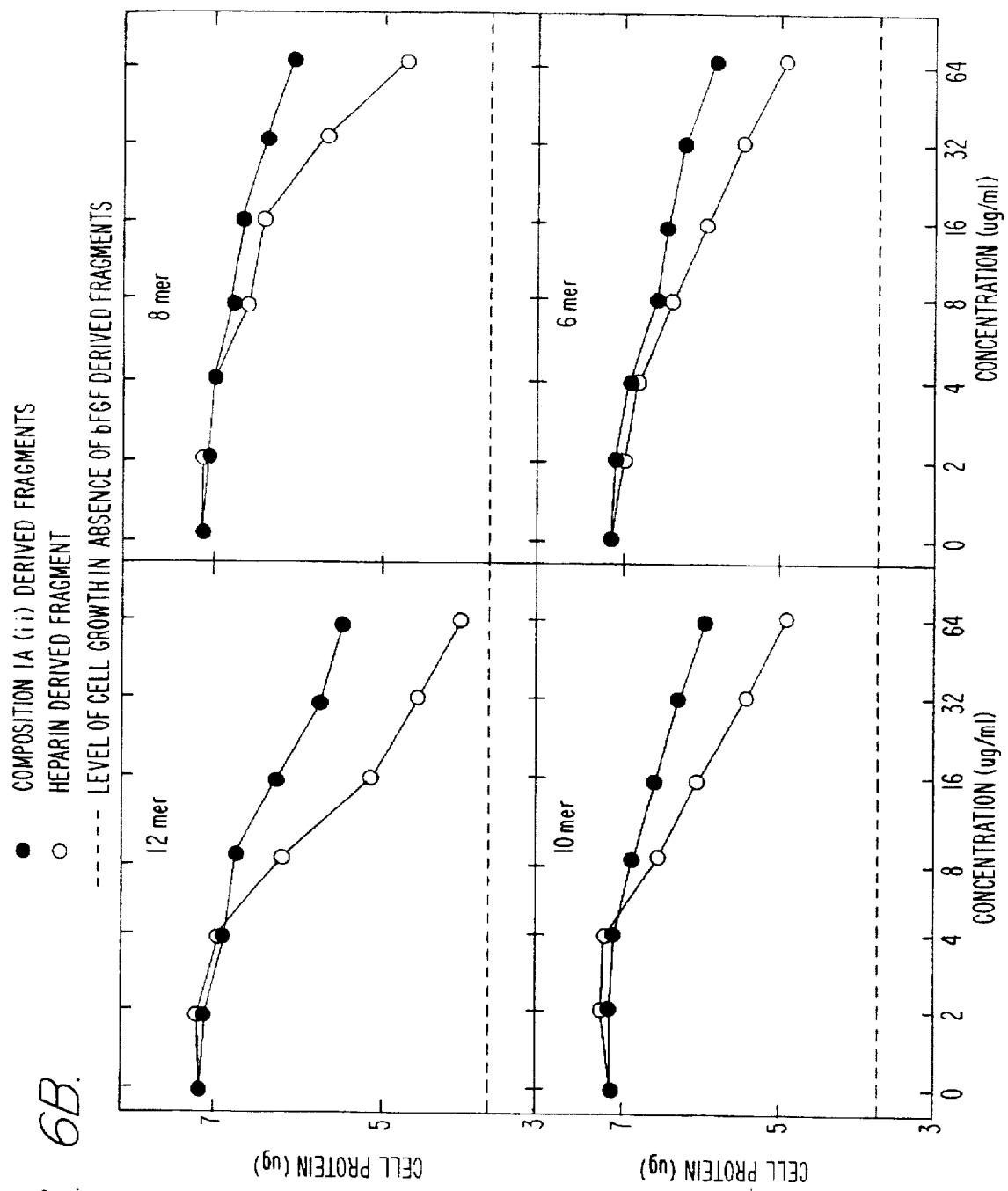
FIG. 6B shows the results of the effect of Composition 1A (ii) in the assay to determine bFGF-induced ACE cell growth. The hexa, octa, deca and dodecamers from Composition 1A (ii) were two fold less active in the inhibition of bFGF-induced ACE cell growth as compared to heparin derived oligo-saccharides.
Figure 6C:
FIG. 6C shows the results of the effect of Composition 1A (ii) in the assay to determine bFGF-induced ACE cell stimulation. The decamers and dodeca-mers of heparin and Composition 1A (ii) showed approximately equivalent activity, while the hexamers and octamers of both were substantially inactive.

These oligomers were characterized to consist mainly of the structure (IdoA2S-GlcNS), while the corresponding oligomers from heparin would be (IdoA2S-GlcNS6S). The hexa, octa, deca and dodecamers from Composition 1A (ii) inhibited bFGF binding to RO-12 UC cells about as well as heparin oligosaccharides (FIG. 6A), but were two fold less active in the inhibition of bFGF-induced ACE cell growth (FIG. 6B). The decamers and dodecamers of heparin and Composition 1A (ii) showed approximately equivalent activity in a bFGF-induced ACE cell stimulation assay, while the hexamers and octamers of both were substantially inactive (FIG. 6C).

TABLE 3

Activity of desulfated heparin derivatives in bFGF Binding Assay

| Composition | aPTT (%) | bFGF binding (IC$_{50}$) | bFGF CGI[a] (µg/ml) | bFGF CGS[b] (ng/ml) |
|---|---|---|---|---|
| Heparin | 100 | <1 | 10 | <100 |
| 1A (i) | 27 | 2.0 | — | — |
| (ii) | 30 | 1.5 | — | — |
| 2A (i) | 7 | ~1 | 32 | ~100 |
| (ii) | 5.2 | 1.5 | — | — |
| (iii) | 11 | 1.0 | — | — |
| 3 (i) | 1.6 | 1.5 | — | — |
| (ii) | 5 | 1.0 | — | — |
| (iii) | 1 | 2.0–3.0 | 30 | 250–500 |
| 3A (ii) | 1.2 | 2.0 | — | — | a = cell growth inhibitor; b = cell growth stimulation

EXAMPLE 5

Effect of Composition 2A (i) on Ristocetin Induced Platelet Aggregation

The effect of Composition 2A (i) on ristocetin induced platelet aggregation was measured in the presence of vWF as described by Sobel et al., *J. Clin. Invest.* (1992) 87:1787–1793, and Kelton et al., *Thromb Res* (1980) 18:477–483.

The experiment was conducted as follows. Platelet-rich plasma was prepared from citrated whole blood of 300–500 gram male guinea-pigs by low speed centrifugation to sediment the red blood cells. The guinea pigs were anesthetized with methoxyflurane. The upper layer was harvested and used to determine the effects of the heparinoids on platelet aggregation. The remaining red blood cell rich plasma was centrifuged at high speed in order to prepare a platelet poor plasma fraction that was used as a blank in the aggregometer. 400 µl samples, consisting of 200 µl of platelet-rich plasma and 200 µl of platelet poor plasma, were placed in the light path of a dual aggregation module (Payton) two-channel aggregometer, and preincubated at 37° C. with various concentrations of heparinoid test material or PBS buffer control for 10 minutes. The samples were continuously stirred at 1,000 rpm. Aggregation was induced by adding 6 µl of ristocetin (stock solution, 125 mg/ml in 0.9% sterile saline) and aggregation recorded as the change in light transmission using the platelet poor plasma as a blank.

Composition 2A (i) and heparin were tested at various concentrations, the highest being 1000 µg/ml, and the remaining being 2 fold serial dilutions.

The results were expressed as the $EC_{70}$ concentrations, or the concentration that was effective at inhibiting 70% aggregation. The $EC_{70}$ concentrations for Composition 2A (i), were expressed relative to heparin which was taken as 1. The $EC_{70}$ concentration for Composition 2A (i) was 0.5.

Thus, Composition 2A(i) inhibits platelet aggregation to a lesser extent, 50%, than heparin indicating possibly reduced bleeding potential.

EXAMPLE 6

Effect of Compositions 2A (iii) and 3 (ii) On Antithrombotic Activities

The anti-Xa activity of Compositions 2A (iii) and 3 (ii), as measured using a chromogenic assay, was dramatically reduced relative to heparin. Derivatives from unfractionated heparins typically had <15% of the activity of the starting heparin. This activity reduction suggests a reduced affinity of these compositions for ATIII, the main inhibitory pathway for Factor Xa.

The anti-IIa activity of Compositions 2A (iii) and 3(ii), as measured using an assay kit and a chromogenic substrate, was dramatically reduced relative to heparin. The various derivatives from unfractionated heparins typically had <5% of the activity of the starting heparin. These results indicate that these compositions had lost affinity for both ATIII and Heparin Cofactor II, the two main mechanisms for inhibition of Factor IIa.

EXAMPLE 7

Anti Restenotic Activity of Composition 1A (ii)

Composition 1 A (ii) was tested for anti restenotic activity by the following assay, using an intravenous (IV) mode of administration.

Sprague Dawley male rats (350–375 g body weight, n=8) were used in all balloon injury experiments.

Osmotic minipumps were prepared by filling with drug or vehicle (lactated Ringer) pre-filtered through a sterile 0.2 µm filter disk. Pump regulators were connected to a length of silastic tubing (0.025"×0.047" i.d.). This procedure was carried out 24 hours prior to implantation in the rats, and 48 hours prior to balloon injury. Pumps were incubated at 37° C. for 18–24 hours prior to implantation. Dosage for the compounds was set at 0.3 mg/kg/hr with a pump rate of 4.99 µl/hr.

On the day prior to balloon injury, animals were anesthetized by inhalation of methoxyflurane followed by intramuscular injection of xylazine 1.4 mg/kg, acepromazine 0.7 mg/kg, and ketamine 36 mg/kg in a volume of 0.7 ml/kg. The cervical and dorsal lumbar regions were shaved.

Using antiseptic procedures, the left common carotid and external carotid arteries were isolated. A balloon catheter was filled with saline and inserted into the left common carotid via the left external common carotid. The catheter was passed as far as the aortic arch (about 4 cm). The catheter was inflated (0.1–0.3 ml) and slowly withdrawn while inflated. The process was repeated a total of three times in the left common carotid. The right common carotid was the control side and was not ballooned (uninjured) or treated with compound.

The left superficial masseter muscle was first located and a tunnel leading to the dorsal side was made using long blunt scissors. The osmotic pump was placed into the tunnel. The left jugular vein was isolated and the catheter from the pump was inserted into the left jugular vein. Sutures were used to hold the catheter and the jugular in place. A reef knot was first tied at the cephalic end followed by the caudal end. A cross tie suture was performed to assure that the jugular and the catheter would remain in place together. Surgical staples were used for closing following surgery.

Animals were anesthetized and heparinized by a bolus intravenous injection of heparin at 80 mg/kg, at a concentration of 80 mg/ml in saline. Animals were euthanized by cutting the heart and the vessels were excised. The left and right common carotids were excised and placed into small petri-dishes (6×1.5 cm) for flushing with 1 ml of Tyrode's solution. Tyrode's solution was placed in a water bath at 37° C. Extraneous connective tissue was removed carefully by teasing with forceps. The vessels were transferred into pre-labelled 15 ml centrifuge tubes containing 1–2 ml of 37% formalin. Vessels were measured in centimeters and were photographed according to animal and vessel types.

One animal died in the test group {animals treated with Composition 1A (ii)} due to bleeding around the insertion site of the tubing for the pump, 4 days after surgery. An additional data point was lost due to technical error.

Figure 7B:
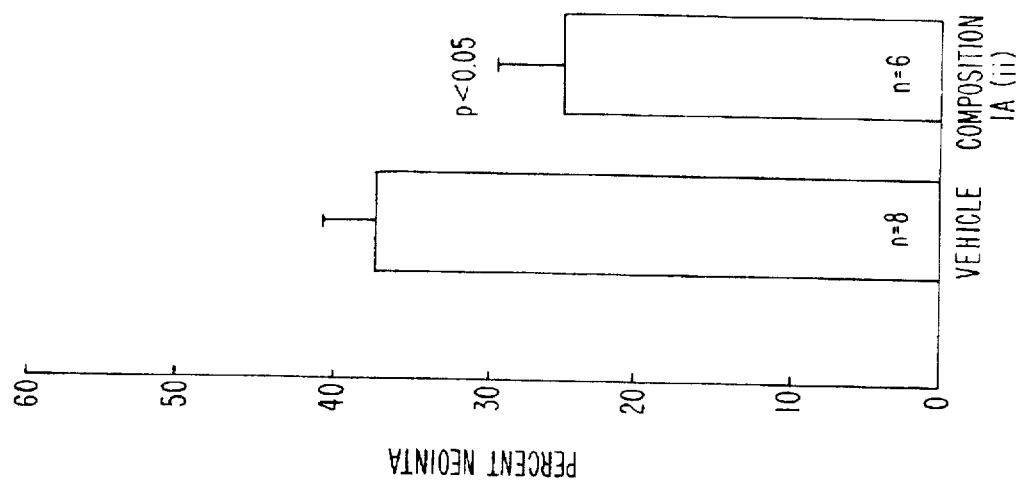
FIG. 7B shows the results of the effect of Composition 1A (ii) in the anti-restenotic assay, plotted as % neointima, with an intravenous route of administration. A 40% reduction in intimal area ($p<0.05$) was observed for animals treated with Composition 1A (ii).
Figure 7A:
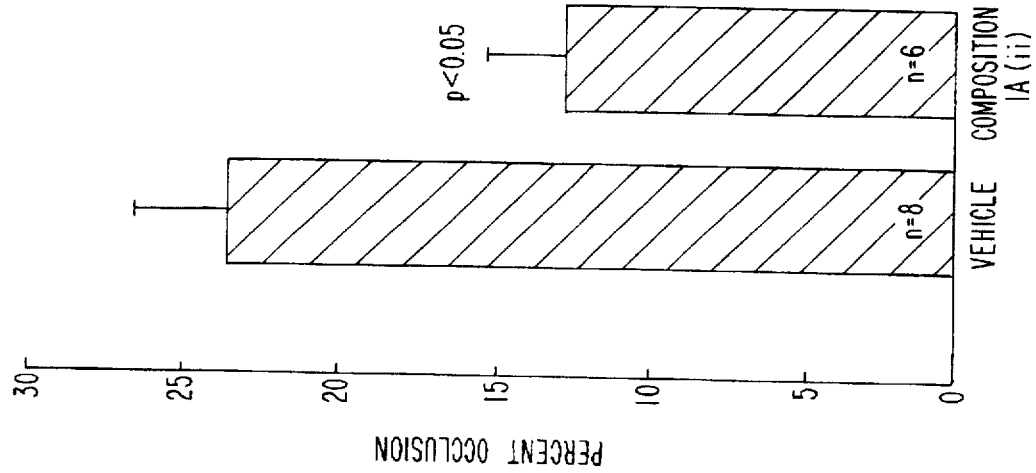
FIG. 7A shows the results of the effect of Composition 1A (ii) in the anti-restenotic assay, plotted as % occlusion, with an intravenous route of administration. A 54% reduction in occlusion ($p<0.05$) was observed for animals treated with Composition 1A (ii).

FIG. 7A shows the results of the effect of Composition 1A (ii) in the anti-restenotic assay, plotted as % occlusion, with an intravenous route of administration. A 54% reduction in occlusion (p<0.05) was observed for animals treated with Composition 1A (ii).

FIG. 7B shows the results of the effect of Composition 1A (ii) in the anti- restenotic assay, plotted as % neointima, with an intravenous route of administration. A 40% reduction in intimal area (p<0.05) was observed for animals treated with Composition 1A (ii).

EXAMPLE 8

Anti-Restenotic Activity Of Composition 2A (ii)

To determine the effectiveness of Composition 2A (ii) in the restenosis assay, given subcutaneously and daily for two weeks.

Male Sprague Dawley rats (350–375 g body weight) obtained from Harlan Laboratories were used in the following experiment. Composition 2A (ii) formulated in lactated Ringers solution was given subcutaneously at a dose of 20 mg/kg/day at the back of the neck. Control animals were given vehicle only. The following day, balloon injury was performed in all animals as described in Example 9. Daily, and for fourteen days, animals received either vehicle or Composition 2A (ii) injections subcutaneously. Fourteen days after balloon injury, animals were sacrificed and left carotid arteries were taken from all animals and submitted for histological sectioning prior to morphological analysis.

Measurements of adventitia, medial, neointimal and lumenal areas were measured directly. Other measurements were calculated exactly as described Example 9.

Figure 8:
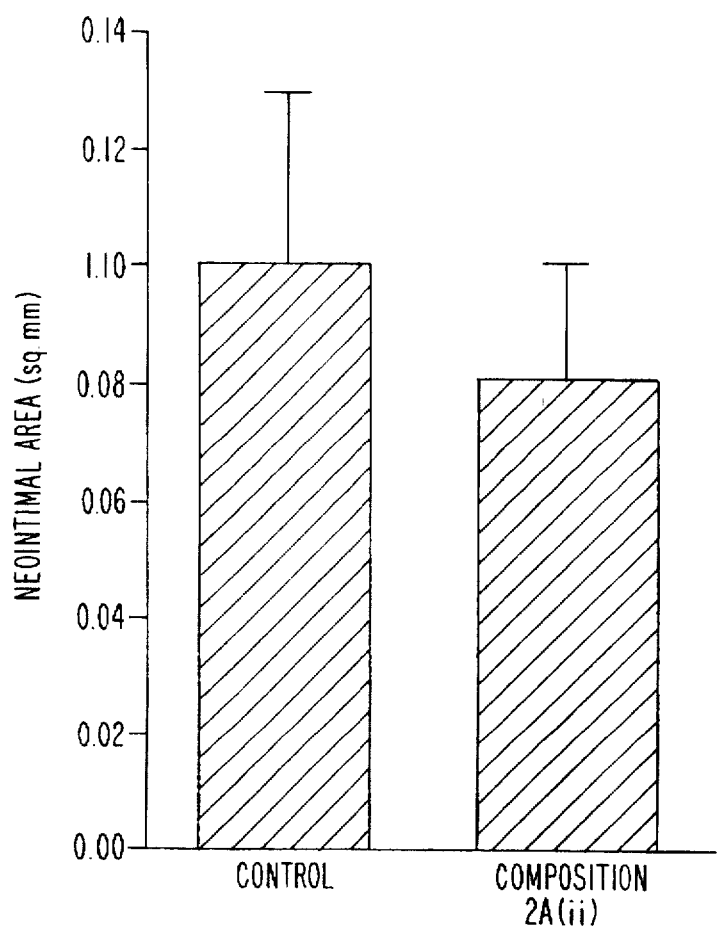
FIG. 8 shows the results of the effect of Composition 2A (ii) in the anti-restenotic assay, with a subcutaneous route of administration. Administration of Composition 2A (ii) causes a reduction in the neointimal area as compared to the vehicle control.

Measurements of neointimal size in carotid arteries 14 days after balloon injury, and following treatment of Composition 2A (ii) indicated that there was a 20% reduction in neointimal area (FIG. 8, Table 5). A similar reduction was observed in percent neointima and percent occlusion in the Composition 2A (ii) treated animals (Table 5).

No indication of adverse effects of Composition 2A (ii) administration subcutaneously such as occluded arteries or intradermal hemorrhage at the injection site was seen in these experimental animals.

TABLE 5

| Parameter | Control | Composition 2A |
| --- | --- | --- |
| Adventitia Area (sq. mm) | 0.25 ± 0.02 | 0.28 ± 0.01 |
| Medial Area (sq. mm) | 0.18 ± 0.01 | 0.19 ± 0.01 |
| Neointimal Area (sq. mm) | 0.10 ± 0.03 | 0.08 ± 0.02 |
| Lumenal Area (sq. mm) | 0.44 ± 0.02 | 0.40 ± 0.02 |
| Percent Neointima (%) | 31.85 ± 6.29 | 27.50 ± 4.20 |
| Lumenal Area as a Circle (sq. mm) | 0.65 ± 0.03 | 0.64 ± 0.04 |
| Percent Occlusion (%) | 15.41 ± 3.90 | 13.89 ± 3.10 |
| Residual lumenal Area (sq. mm) | 0.54 ± 0.02 | 0.56 ± 0.05 |
| Arterial Cross Sectional Area (sq. mm) | 0.82 ± 0.03 | 0.83 ± 0.04 |
| Arterial Diameter (mm) | 1.02 ± 0.0 | 1.02 ± 0.0 |

EXAMPLE 9

Anti Restenotic Activity of Composition 2A (ii)

The effectiveness of the Composition 2A (ii) would be shown to be useful to treat or prevent anti-restenotic activity using an IV mode of administration as described in Example 9.

Sprague Dawley male rats (350–375 g body weight) would be used in balloon injury experiments.

Osmotic minipumps are prepared by filling with drug or vehicle (lactated Ringer) pre-filtered through a sterile 0.2 μm filter disk. Pump regulators are connected to a length of silastic tubing (0.025"×0.047" i.d.). This procedure is carried out 24 hours prior to implantation in the rats, and 48 hours prior to balloon injury. Pumps are incubated at 37° C. for 18–24 hours prior to implantation. Dosage for the compounds is set at 0.3 mg/kg/hr with a pump rate of 4.99 μl/hr.

On the day prior to balloon injury, animals are anesthetized by inhalation of methoxyflurane followed by intramuscular injection of xylazine 1.4 mg/kg, acepromazine 0.7 mg/kg, and ketamine 36 mg/kg in a volume of 0.7 ml/kg. The cervical and dorsal lumbar regions are shaved.

Using antiseptic procedures, the left common carotid and external carotid arteries are isolated. A balloon catheter is filled with saline and inserted into the left common carotid via the left external common carotid. The catheter is passed as far as the aortic arch (about 4 cm). The catheter is inflated (0.1–0.3 ml) and slowly withdrawn while inflated. The process is repeated a total of three times in the left common carotid. The right common carotid is the control side and is not ballooned (uninjured) or treated with compound.

The left superficial masseter muscle is first located and a tunnel leading to the dorsal side is made using long blunt scissors. The osmotic pump is placed into the tunnel. The left jugular vein is isolated and the catheter from the pump is inserted into the left jugular vein. Sutures are used to hold the catheter and the jugular in place. A reef knot is first tied at the cephalic end followed by the caudal end. A cross tie suture is performed to assure that the jugular and the catheter would remain in place together. Surgical staples are used for closing following surgery.

Animals are anesthetized and heparinized by a bolus intravenous injection of heparin at 80 mg/kg, at a concentration of 80 mg/ml in saline. Animals are euthanized by cutting the heart and the vessels are excised. The left and the right common carotids are excised and placed into small petridishes (6×1.5 cm) for flushing with 1 ml of Tyrode's solution. Tyrode's solution is placed in a water bath at 37° C. Extraneous connective tissue is removed carefully by teasing with forceps. The vessels are transferred into pre-labelled 15 ml centrifuge tubes containing 1–2 ml of 37% formalin. Vessels are measured in centimeters and are photographed according to animal and vessel types.

A significant reduction in occlusion and intimal area would be observed for animals treated with Composition 2A (ii). Composition 2A (ii) would be considerably useful to treat or prevent anti-restenotic activity using an IV mode of administration. These findings would support those in the previous examples, and stresses the multiple modes of administration of the invention compounds.

Having described what the applicants believe their invention to be, a skilled practitioner of this art should not construe the invention to be limited other that by the scope of the appended claims.

What is claimed is:

1. A method for inhibiting angiogenesis or treating a disease selected from the group consisting of cancer, ischemia reperfusion injury, inflammation, restenosis, and cardiovascular diseases, in an animal host, comprising administering to said animal host an effective amount of a composition comprising a substantially unfragmented N-sulfated 6-O-desulfated heparin, or an N-sulfated 6-O-desulfated heparin fragment, which heparin or heparin fragment has less than 30% of the anticoagulant activity of unmodified heparin.

2. The method of claim 1 wherein said heparin or heparin fragment is less than approximately 34% 6-O-sulfated and up to about 67% 2-O-sulfated.

3. A method for inhibiting heparanase, comprising contacting said heparanase with an effective amount of a composition comprising a substantially unfragmented N-sulfated 6-O-desulfated heparin or an N-sulfated 6-O-desulfated heparin fragment, which heparin or heparin fragment has less than 30% of the anticoagulant activity of unmodified heparin.

4. The method of claim 3 wherein said heparin or heparin fragment is less than approximately 34% 6-O-sulfated and up to about 67% 2-O-sulfated.

5. A method for inhibiting angiogenesis in an animal suffering from unwanted angiogenesis, comprising administering to said animal an effective amount of a composition comprising a substantially unfragmented N-sulfated 6-O-desulfated heparin or an N-sulfated 6-O-desulfated heparin fragment which heparin or heparin fragment has less than 30% of the anticoagulant activity of unmodified heparin.

6. The method of claim 5 wherein said heparin or heparin fragments are less than approximately 34% 6-O-sulfated and up to about 67% 2-O-sulfated.

7. The method of claim 2 wherein said heparin or heparin fragment is less than 34% 6-O-sulfated and up to 67% 2-O-sulfated.

8. The method of claim 7 wherein said heparin or heparin fragment is 12–26% 6-O-sulfated and 28–50% 2-O-sulfated.

9. The method of claim 7 wherein said heparin or heparin fragment is less than 13% 6-O-sulfated and 14–18% 2-O-sulfated.

10. The method of claim 4 wherein said heparin or heparin fragment is less than 34% 6-O-sulfated and up to 67% 2-O-sulfated.

11. The method of claim 10 wherein said heparin or heparin fragment is 12–26% 6-O-sulfated and 28–50% 2-O-sulfated.

12. The method of claim 10 wherein said heparin or heparin fragment is less than 13% 6-O-sulfated and 14–18% 2-O-sulfated.

13. The method of claim 6 wherein said heparin or heparin fragment is less than 34% 6-O-sulfated and up to 67% 2-O-sulfated.

14. The method of claim 13 wherein said heparin or heparin fragment is 12–26% 6-O-sulfated and 28–50% 2-O-sulfated.

15. The method of claim 13 wherein said heparin or heparin fragment is less than 13% 6-O-sulfated and 14–18% 2-O-sulfated.

16. The method of claim 7 wherein said composition is administered orally, subcutaneously, or intravenously.

* * * * *